United States Patent [19]
Hathaway et al.

[11] Patent Number: 6,132,440
[45] Date of Patent: Oct. 17, 2000

[54] APPARATUS AND METHOD FOR POSITIVE CLOSURE OF AN INTERNAL TISSUE MEMBRANE OPENING

[75] Inventors: David Hathaway, Indianapolis; Brian Patton, Thorntown; Keith March, Carmel, all of Ind.

[73] Assignee: Advanced Research & Technology Institute, Bloomington, Ind.

[21] Appl. No.: 09/158,446

[22] Filed: Sep. 22, 1998

Related U.S. Application Data

[63] Continuation of application No. 08/935,848, Sep. 23, 1997, Pat. No. 5,810,850, which is a continuation of application No. 08/465,765, Jun. 6, 1995, Pat. No. 5,720,757, which is a continuation of application No. 08/194,072, Feb. 9, 1994, Pat. No. 5,476,469, which is a continuation of application No. 07/963,053, Oct. 19, 1992, Pat. No. 5,304,184.

[51] Int. Cl.[7] .................................................... A61B 17/04
[52] U.S. Cl. .......................................... 606/144; 606/148
[58] Field of Search ...................................... 606/144, 148

[56] References Cited

U.S. PATENT DOCUMENTS

| | | | |
|---|---|---|---|
| 2,397,823 | 4/1946 | Walter | 128/321 |
| 4,168,073 | 9/1979 | LaRue | 279/2 |
| 4,437,465 | 3/1984 | Nomoto et al. | 128/340 |
| 4,493,323 | 1/1985 | Albright et al. | 128/340 |
| 4,836,205 | 6/1989 | Barrett | 128/340 |
| 4,898,155 | 2/1990 | Ovil et al. | 606/144 |
| 4,957,498 | 9/1990 | Caspari et al. | 606/146 |
| 5,037,433 | 8/1991 | Wilk et al. | 606/139 |
| 5,304,184 | 4/1994 | Hathaway et al. | 606/144 |
| 5,476,469 | 12/1995 | Hathaway et al. | 606/144 |

FOREIGN PATENT DOCUMENTS 1093329  5/1984  Russian Federation.

*Primary Examiner*—Michael Buiz
*Attorney, Agent, or Firm*—Woodard, Emhardt, Naughton Moriarty & McNett

[57] ABSTRACT

The invention provides a device having two components: a needle advancing apparatus slidable longitudinally along a catheter to advance needles into a tissue membrane, such as a blood vessel wall, around an opening in the membrane; and, a suture retrieval assembly insertable through the catheter beyond a distal side of the tissue membrane. The needle advancing apparatus advances suture through the tissue wall. The suture retrieval assembly grabs the suture on the distal side of the tissue membrane for extraction thereof through the opening in the tissue membrane. A method for suturing a membrane beneath the patient's skin is also disclosed.

3 Claims, 28 Drawing Sheets

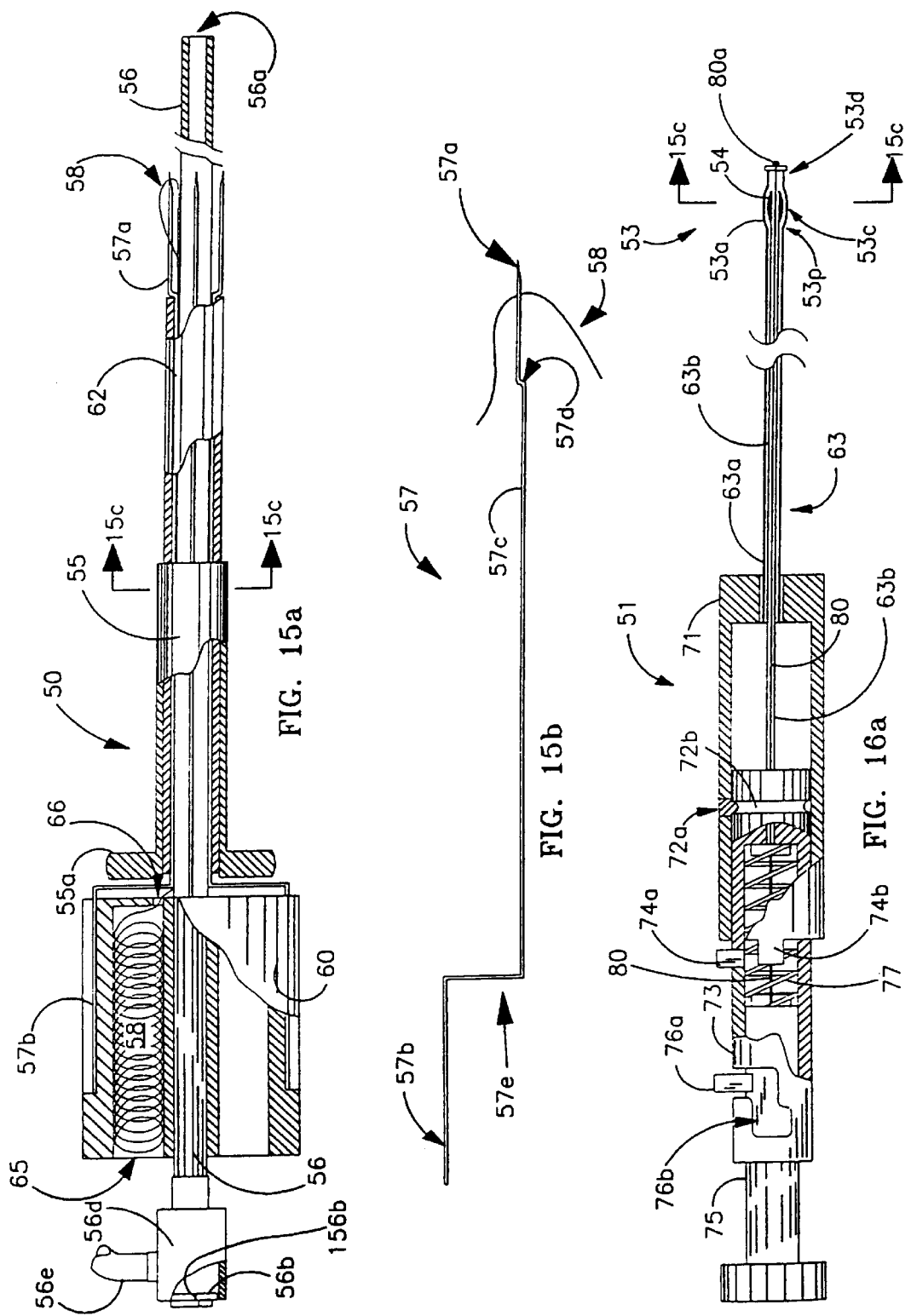

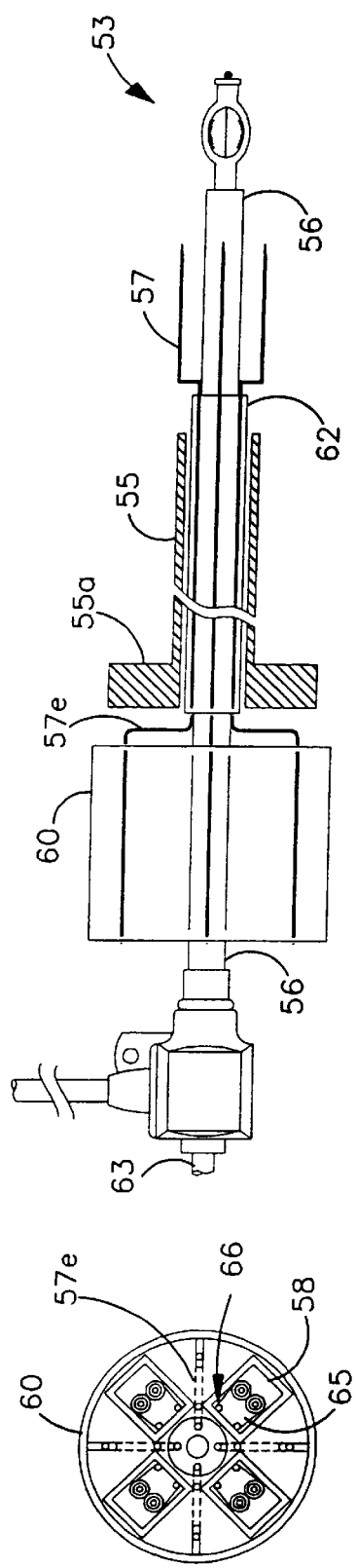
FIG. 17a
FIG. 17b
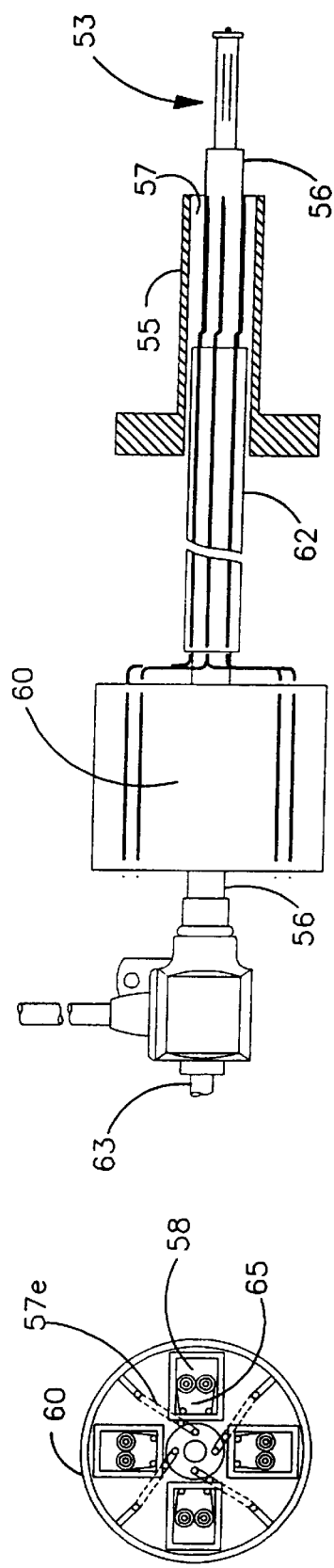
FIG. 17c
FIG. 17d

APPARATUS AND METHOD FOR POSITIVE CLOSURE OF AN INTERNAL TISSUE MEMBRANE OPENING

This application is a continuation of application Ser. No. 08/935,848, filed Sep. 23, 1997, now U.S. Pat. No. 5,810,850; which is a continuation of application Ser. No. 08/465,765, filed Jun. 6, 1995, now U.S. Pat. No. 5,720,757; which is a continuation of application Ser. No. 08/194,072, filed Feb. 9, 1994, now U.S. Pat. No. 5,476,469; which is a continuation of application Ser. No. 07/963,053, filed Oct. 19, 1992, now U.S. Pat. No. 5,304,184.

BACKGROUND OF THE INVENTION

The present invention relates generally to an apparatus method for closure, such as by suturing, of tissue membrane openings. The present invention has particular application in the closure of openings in blood vessel walls after catheterization procedures in the cardiovascular system have been performed.

A wide variety of techniques have been employed to provide nonsurgical, less invasive procedures in a medical patient. These include laparoscopy, arthroscopy, and various other techniques in which surgical and/or medicational procedures are performed via tubes, such as catheters, rather than full-scale "cut down" surgery. One such technique is the Seldinger technique involving the placement of guide wires and catheters in the cardiovascular system of the patient. Although such nonsurgical procedures typically greatly enhance the recovery time of the patient when compared to more conventional cut down surgery, nevertheless, openings formed in tissue membranes, such as arterial walls, take time to heal.

Prior methods and devices typically involve placement of collagen external to the puncture wound with or without the placement of a polylactide member internal to the puncture wound such as in the lumen of the blood vessel. Potential problems with this approach involve the increase in thrombosis that has been observed to follow placement of a permanent in intravascular device, the known effects of collagen to activate platelets and consequently induce thrombosis, and the occurrence of a systemic auto-immune inflammmatory response following implants of bulk collagen.

By way of background, other suturing and stitching devices and methods are disclosed in the following U.S. Pat. Nos. 5,037,433 to Wilk et al., 4,957,498 to Caspari et al., 4,836,205 to Barrett, 4,437,465 to Nomoto et al., and 4,898,155 to Ovil et al..

The present invention provides a suture-based method of closure which circumvents the need for placement of any large piece, such as a stent, within the blood vessel, avoiding attendant risks of thrombosis. Additionally, use of collagens can be avoided, reducing the risk of thrombosis or of an inflammatory autoimmune reaction. The present invention provides these advantages while being usable in the context of noninvasive techniques such as laparoscopy, cardiovascular procedures, or other procedures avoiding conventional cut down surgery, thereby providing the benefits without the necessity for direct visualization of the opening in the tissue which is to be closed. Additionally, the present invention provides substantially reduced healing times for medical patients, reducing patient discomfort and risk and also reducing hospital and personnel costs associated with prolonged healing.

BRIEF DESCRIPTION OF THE DRAWINGS

FIG. 15a illustrates a partially cutaway side view of one embodiment of a needle advancing apparatus according to the present invention.

FIG. 15b illustrates a side view of one needle of FIG. 15a shown in isolation.

FIG. 16a illustrates a partially cutaway side view of one embodiment of a suture retrieval assembly according to the present invention.

FIG. 17a illustrates the present invention with the needle sheath retracted, the needles in a deployed mode, and the distal end of the retrieval assembly in an expanded mode.

FIG. 17b is a rear cutaway view of the suture magazine 60 of FIG. 17a showing the needle crank portions in phantom lines.

FIG. 17c illustrates the present invention with the needle sheath advanced, the needles in a compact mode, and the distal end of the retrieval assembly in a contracted mode.

FIG. 17d is a rear cutaway view of the suture magazine 60 of FIG. 17c showing the needle crank portion in phantom lines.

SUMMARY OF THE INVENTION

Figure 1:
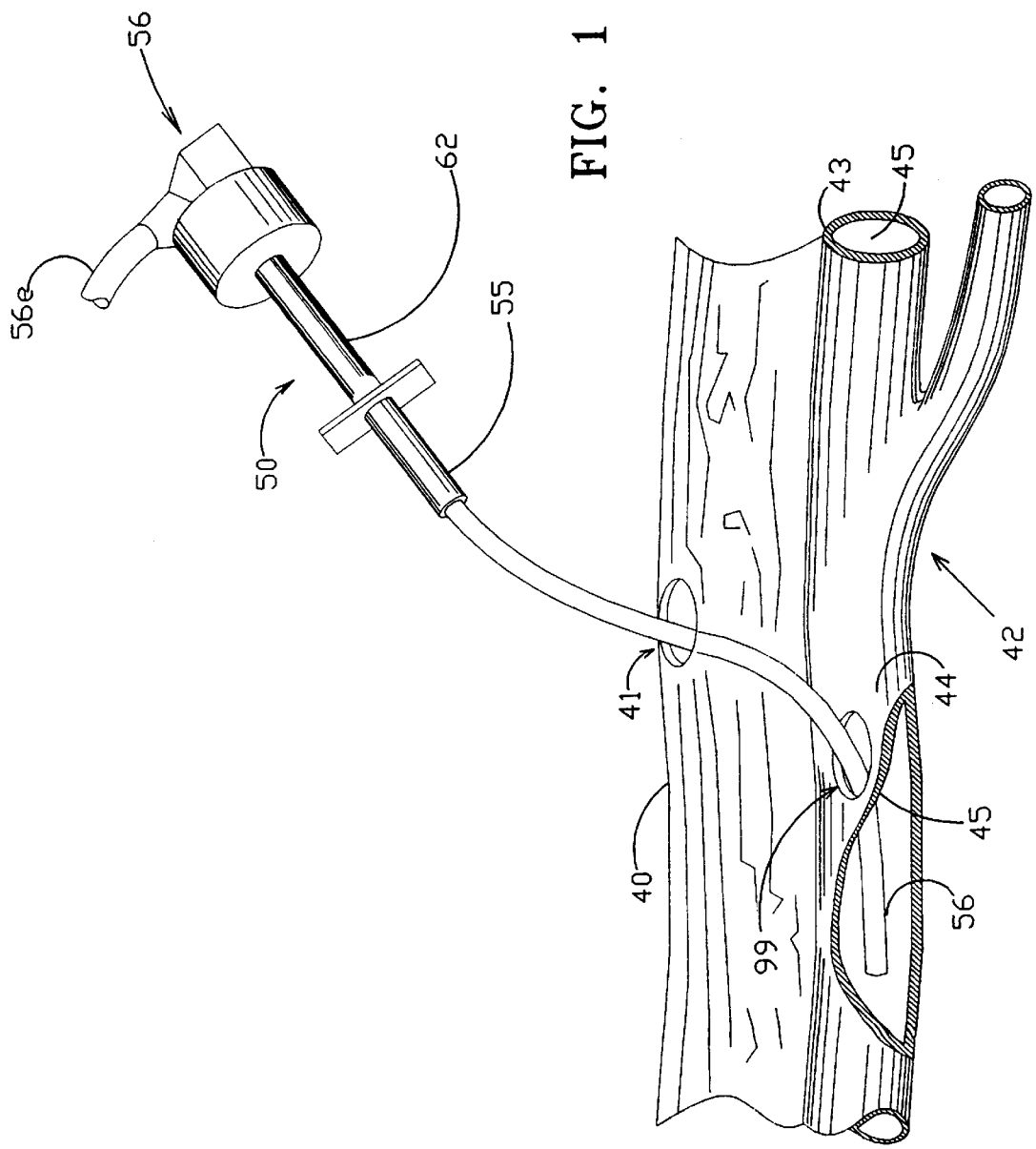
FIGS. 1–13 sequentially illustrate one embodiment of the method according to the present invention to place sutures in a tissue membrane.
Figure 2:
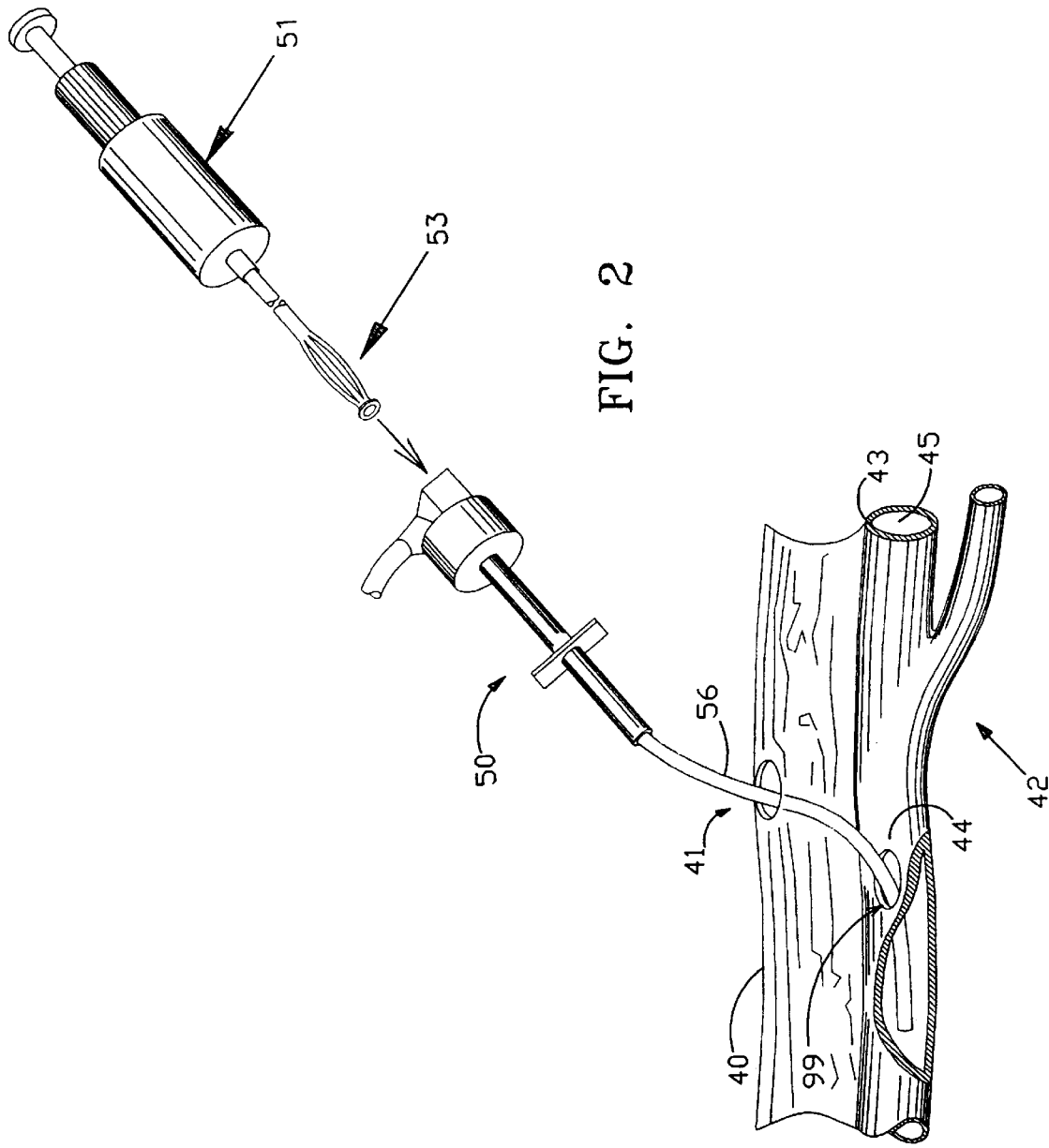
Figure 3:
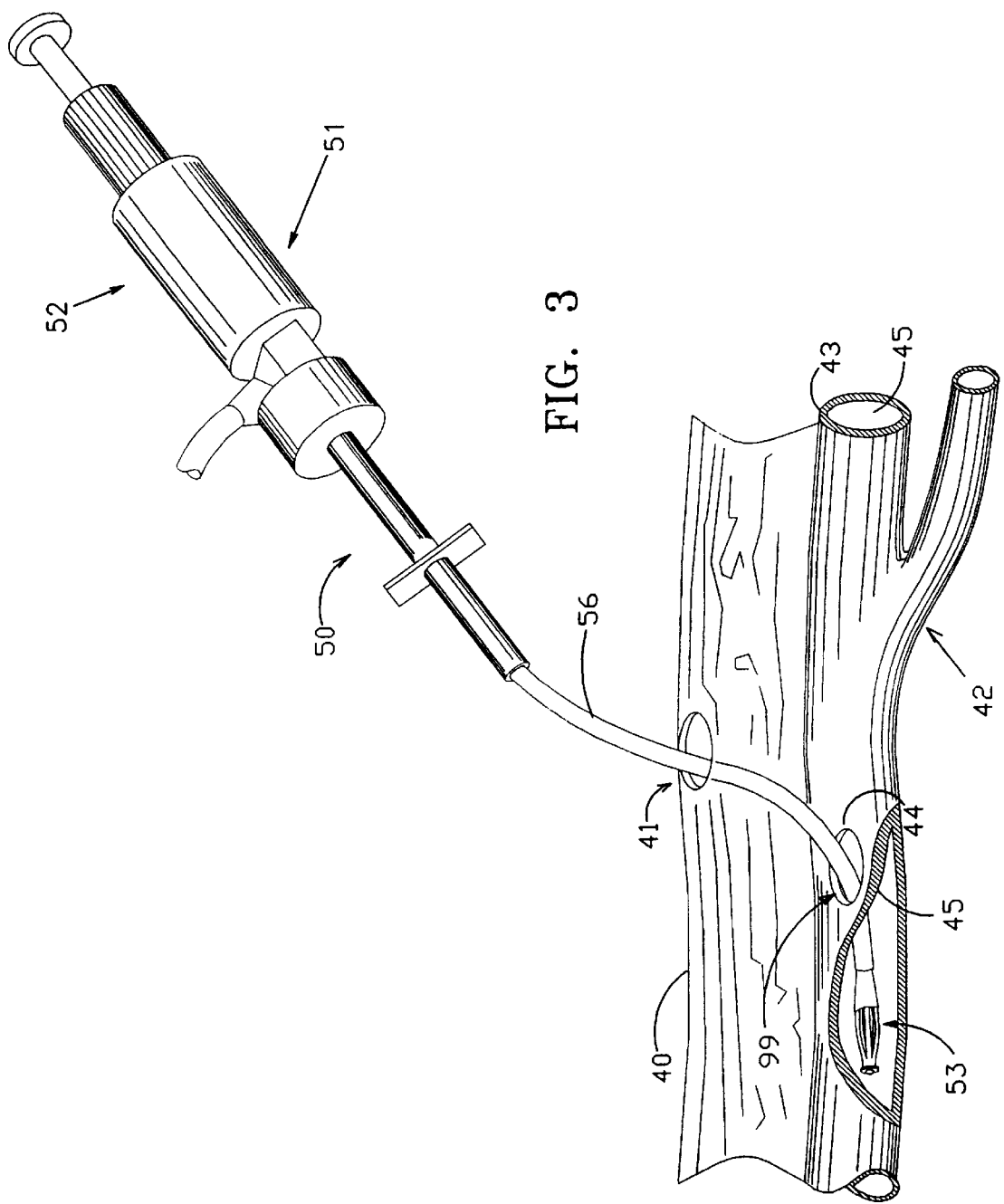
Figure 4:
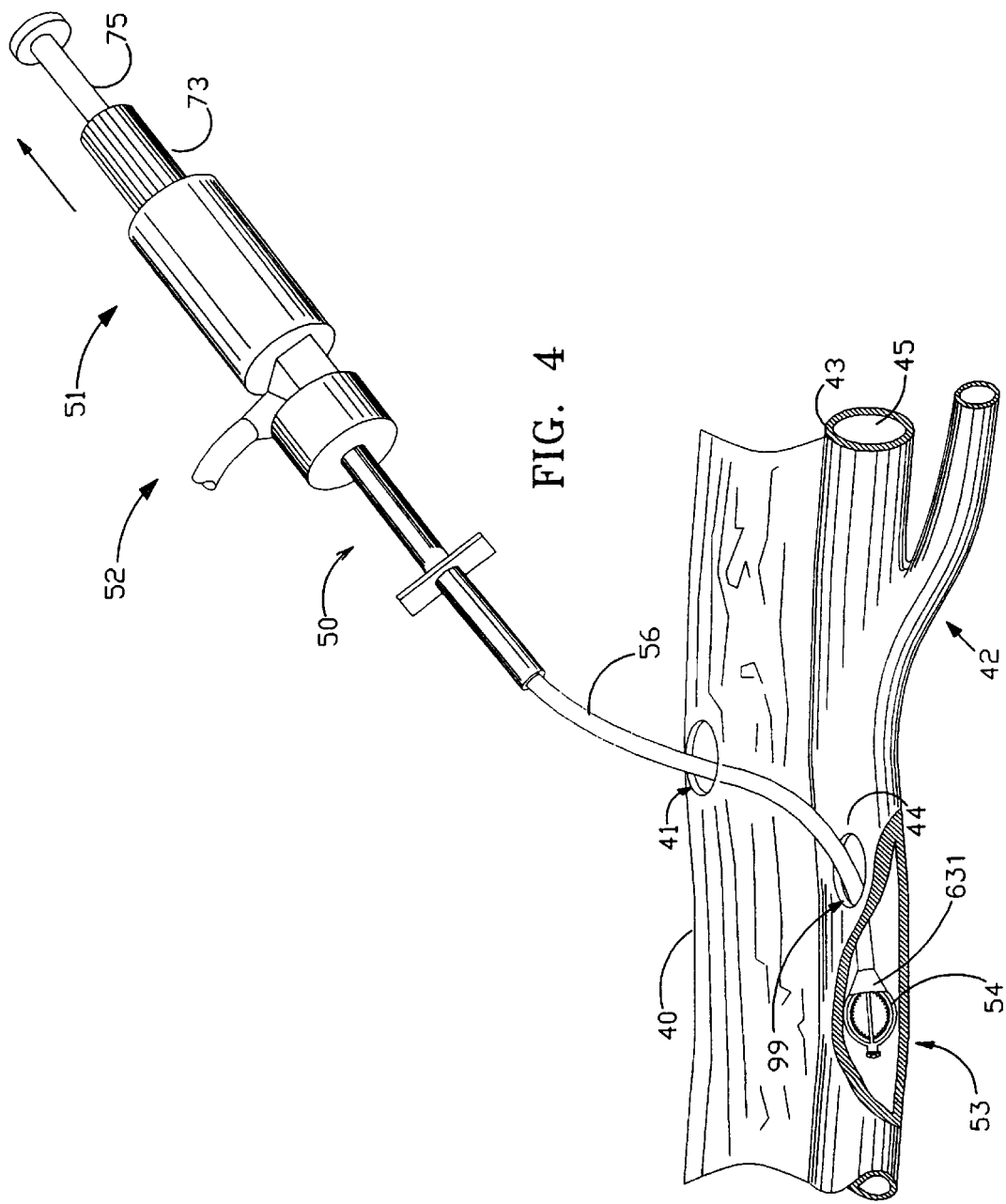

According to one embodiment, the present invention provides a nonsurgical method for closure of an opening in a tissue membrane beneath the skin of a patient. The method includes the steps of providing a tubular member having a lumen therein beneath the skin of the patient and in close proximity to and preferably protruding through the opening; inserting a retrieval assembly through the lumen and past the opening to a location on distal side of the tissue membrane; advancing needle means for passing sutures through the tissue membrane at separate suture locations around the opening; grabbing the sutures with the retrieval assembly on the distal side of the tissue membrane; retrieving the sutures through the opening by withdrawing the retrieval assembly out through the opening; and, drawing together the suture location with the sutures.

According to another embodiment, the present invention provides an apparatus for passing sutures through a tissue membrane located beneath the skin of a patient around an opening in the tissue membrane. The apparatus includes a tubular body having a side wall defining a lumen therein. The tubular body allows introduction of material into the patient through the lumen beyond the tissue membrane. The apparatus further includes array of at least two needles disposed around the tubular body which carry a respective length of suture. The array of needles is advanceable through the tissue to a distal side thereof to provide sutures at separate suture locations in the tissue membrane around the opening.

According to another embodiment, the present invention provides an apparatus for retrieving sutures, alone or in combination with the previously described apparatus, comprising a retrieval assembly having an elongated portion having a first end. The first end includes at least one flexible bow having a distal end, a proximal end, and a central portion therebetween. The apparatus further includes a tension member attached to the distal end of the bow member. The tension member and the proximal end of the bow are selectively movable with respect to each other to urge the distal end and the proximal end towards each other and apart from each other, causing the central portion of the bow to deflect outwardly away from the tension member to receive sutures, and to deflect inwardly toward the tension member in a collapsed position to secure sutures at the first end. The first end in the collapse position is sized to be withdrawn through a catheter lumen.

One object of the present invention is to provide an improved apparatus and method for positive closure of a subcutaneous tissue membrane opening.

Another object of the present invention is to provide closure of tissue membrane openings, such as punctures in blood vessels.

Another object of the present invention is to reduce the need for the use of collagens and/or intravascular devices, such as stents, for closure of puncture wounds.

A further object of the present invention is to reduce the clotting time and the healing time required for a puncture wound in a tissue membrane.

These and other objects and advantages of the present invention will be apparent from the written description and drawing figures herein.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

The present invention provides for the closure of openings in tissue membranes beneath the skin of a medical patient. The invention is useful, for example, to close the opening in the wall of a blood vessel caused by catheterization procedures. The invention is advantageous in that it allows closure of such openings without the need to surgically cut open the patient to visualize the closure procedure. In addition to closure of openings in blood vessels, the invention is useful for closing a variety of openings in various tissue membranes beneath the skin of a patient. Regarding the terminology herein, "distal" means toward the patient and away from the operator (doctor), and conversely "proximal" means toward the operator and away from the patient.

The general procedure of the invention begins with the placement of a catheter through the opening in the tissue membrane. A retrieval device is inserted through the catheter and beyond the opening to the distal side of the membrane. The distal end of the retrieval device is expanded and pulled tightly against the inside surface of the tissue membrane. Thereafter, one or more needles carrying sutures are inserted through the tissue membrane around the opening. The retrieval device grabs the sutures on the distal side of the membrane. The retrieval device is then contracted an removed through the catheter, pulling the sutures with it. Thereafter, knots are formed in the sutures to draw the opening closed for healing. The preferred embodiment of the present invention has two primary components, retrieval assembly 51 (see FIG. 16) and needle advancing apparatus 50 (see FIG. 15a). Collectively, these form the suturing device 52.

Referring to FIGS. 1–13 and FIGS. 14a–14f, a representative illustration of the present inventive method is illustrated for positive closure of opening 99 in tissue membrane 43 of blood vessel 42. The blood vessels located beneath the skin 40 of a medical patient, and is accessed through opening 41 in the skin. Note that the side wall of blood vessel 42 is illustrated partially cut away to facilitate illustration of the method, it being understood that ordinarily the method is performed only with opening 99 in tissue membrane 43. Tissue membrane 43 has a proximal side or surface 44 on the outside thereof and an opposite distal side or surface 45 on the inside thereof as illustrated. While the present invention is illustrated for repairing blood vessel 42, it is to be understood that the present invention may have applicability in positive closure of openings in other tissue membranes in a medical patient which are located beneath the surface of the skin. Such openings may include openings caused by medical procedures, such as laparoscopy, angiography, and others, as well as openings caused by traumatic wounds, including puncture wounds.

FIG. 1 illustrates blood vessel 42 having a sheath 56, such as a catheter, passing through opening 41 and opening 99 and into the interior lumen of the blood vessel, beyond distal side 45. Sheath 56 includes a side wall defining one or more lumens therein as is well known. Sheath 56 typically may be initially placed in blood vessel 42 to facilitate introduction of material into the blood vessel, such as guide wires, catheters, scopes, dilators, inflatable balloons, or any other medical appliance, as well as introduction and/or removal of fluids such as blood, medication, and/or contrast media. In one application, the present inventive method is typically employed after such techniques and/or procedures, referred to herein generally as catheterization procedures, are completed and such medical devices have been removed from sheath 56.

Needle advancing apparatus 50 is illustrated in FIG. 1 disposed around the outside of the side wall of sheath 56, and slideable longitudinally along the length thereof. Apparatus 50 is described in greater detail below. Apparatus 50 includes a tubular member 62 having a side wall defining a lumen therein with an array of needles disposed around sheath 56 protected by a needle guard 55. The needles each have respective lengths of sutures attached thereto.

The distal end 53 of retrieval assembly 51 is inserted (FIG. 2) into the proximal end of the lumen of sheath 56. Retrieval device 51 is fully inserted into sheath 56 (FIG. 3) to position the distal end 53 beyond the distal end of sheath 56 and on the distal side of the membrane 43. The distal end of the retrieval assembly is initially in a collapsed state, being size with a cross-sectional dimension to allow insertion and withdrawal of distal end 53 through the lumen of sheath 56.

Distal end 53 is then expanded within blood vessel 42 (FIG. 4) on the distal side of membrane 43. The expanded state in this embodiment is formed by a plurality of bows, such as bow member 54, which are bulged outwardly. In this particular embodiment the configuration is analogous to an expandable bolt used to anchor fixtures to a building wall. The mechanic of this expansion are described more fully below, but generally are caused by manipulating two-handle members at the proximal end of retrieval assembly 51, namely by rotational release of spring-loaded and/or screw threaded handles, such as movement of handle 75 with respect to handle 73 as shown by the arrow. The distal end preferably includes an expandable outer member and an inner member which rotates within the outer member.

Figure 5:
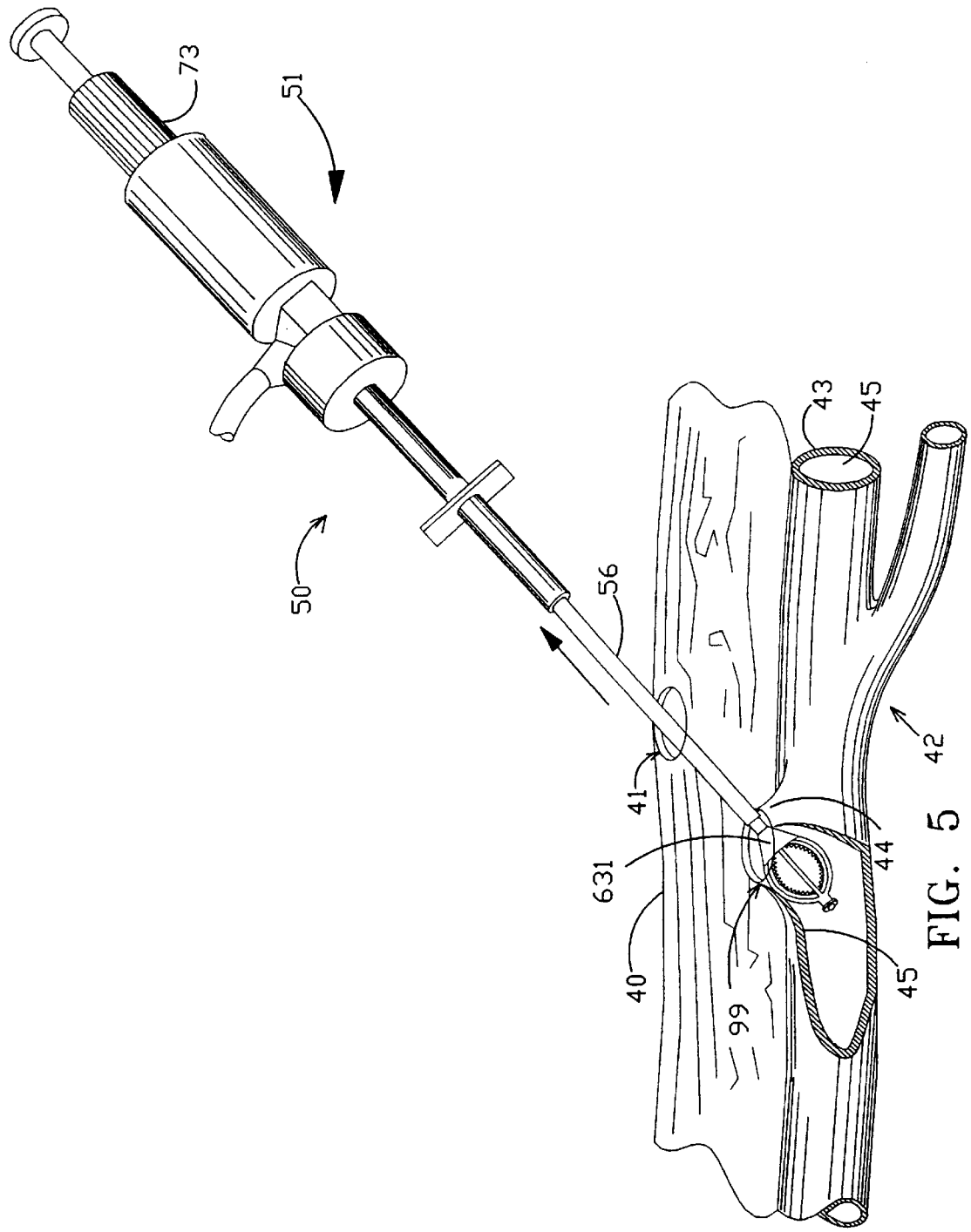
Figure 6:
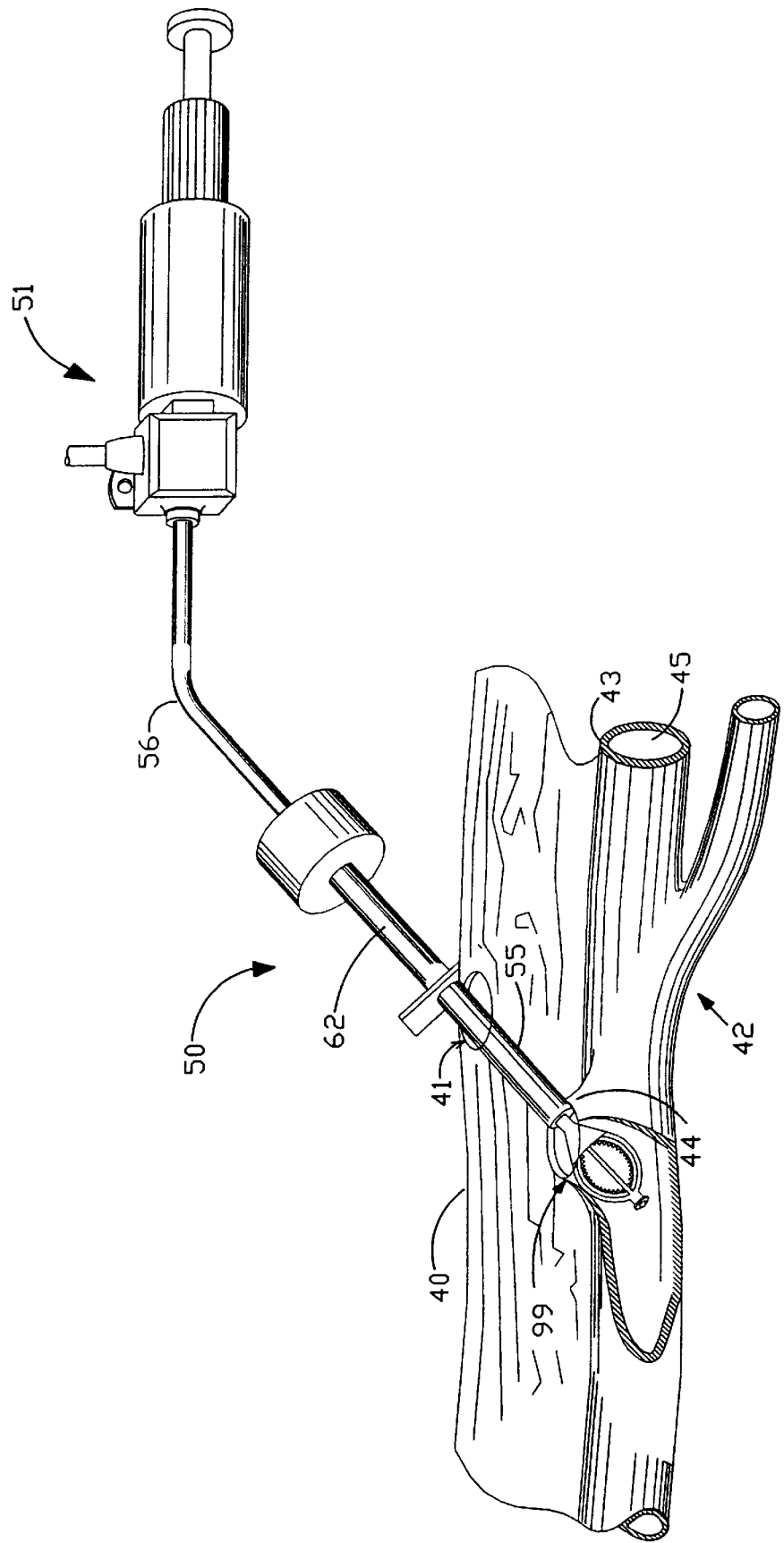

Distal end 53 is expanded and urged against the distal side 45 of the tissue membrane (FIG. 5). Such urging is preferably accomplished by pulling on handle 73, which is connected to distal end 53, in the direction of the arrow. By urging the distal end against the distal side of the tissue (e.g., against the inside of the blood vessel) the blood vessel is distended somewhat and held relatively stationary to facilitate insertion of the suture carrying needles through the tissue membrane. A hemostasis seal member, such as boot 631 (see FIGS. 4 and 5) described further below, seals opening 99 against outflow of fluid such as blood during the procedure.

Needle advancing apparatus 50 is advanced forwardly along sheath 56 towards opening 99. It is slid far enough forward (i.e., distally) so that needle guard 55 passes through opening 41 in the skin, with the distal edge of the needle guard near opening 99 in the blood vessel (see FIG. 6). In this position, the needle guard is poised to be withdrawn, exposing the needles in close proximity to opening 99.

The needle guard 55 is then withdrawn (FIG. 7) by sliding it along tube member 62 (which surrounds sheath 56) to expose the suturing needles, such as needle 57. In the illustrated embodiment, apparatus 50 includes four such needles arrayed equidistantly around sheath 56 for insertion into the tissue membrane around opening 99. The needles are initially a compact mode.

Figure 7:
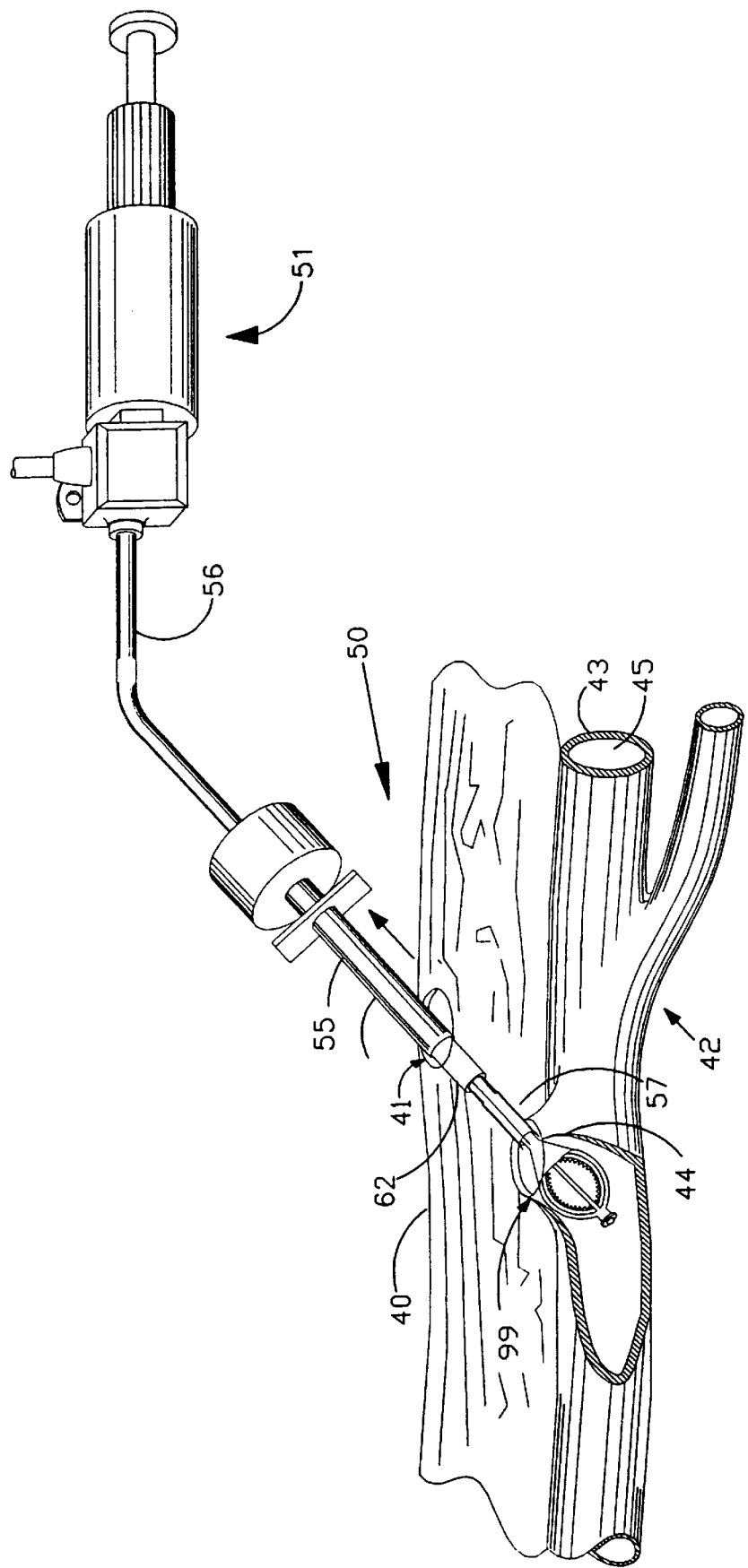
Figure 8:
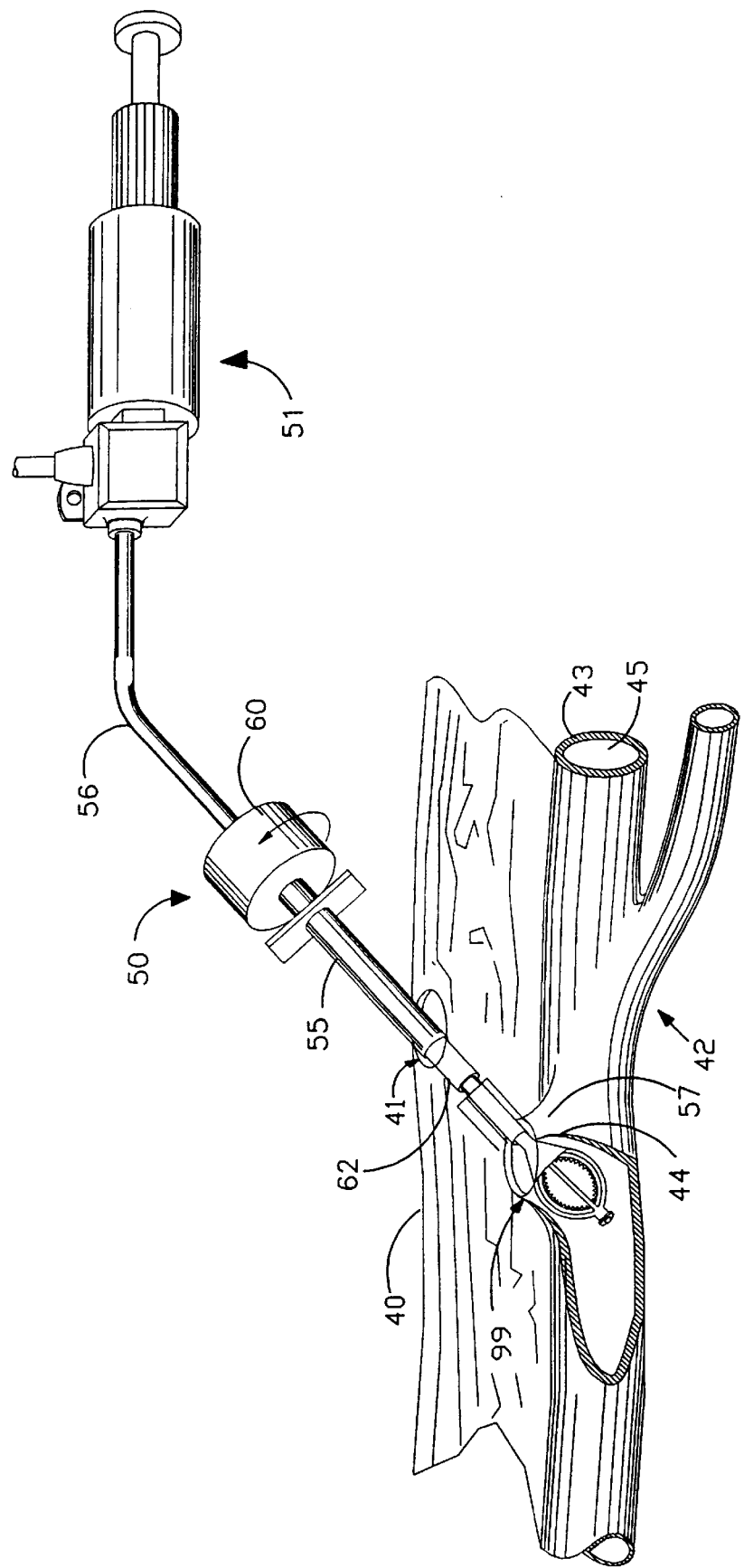

The needles, such as needle 57, are then moved radially outwardly (FIG. 8) (not to scale) away from their relatively radially compact position illustrated in FIG. 7. The manner of deployment in the preferred embodiment is described further below, but generally is caused by ninety degree rotation of a suture magazine 60 with respect to tubular member 62 as shown by the arrow. The needles are arranged as a cranking mechanism which, in response to rotation of magazine 60, causes the needles to move radially outward. In this way, the needles are better radially spaced to allow insertion in the tissue membrane around the circumference of opening 99. It is to be understood that this crank mechanism is only one approach, and other approaches of radially deploying the needles may be utilized, such as spring biased needles with spring outwardly.

Figure 9:
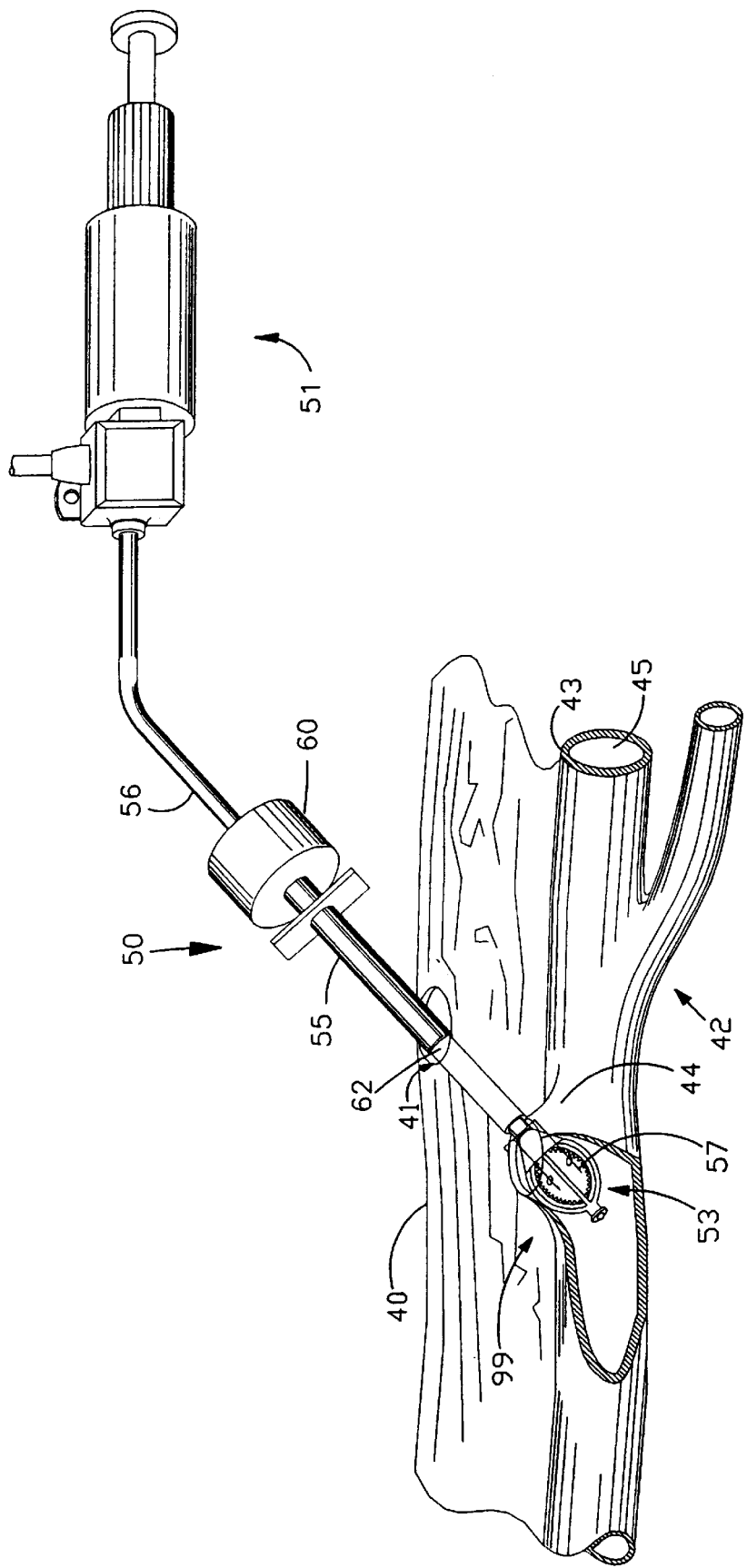

The needles, such as needle 57, are then advanced through the tissue membrane (see FIG. 9). This is caused by forward (i.e. distal) movement of apparatus 50 along sheath 56. The needles are advanced through the tissue membrane at various suture locations caused by the puncturing action of the needles. The needles carry suture or other suitable surgical closure materials. In the preferred embodiment, each needle is a solid stylet with an eyelet near its distal tip carrying a doubled-back length of suture 58 (see FIG. 15b). Accordingly, four lengths of suture, each doubled-back, are simultaneously advanced through the tissue membrane from proximal size 43 to distal side 45. The sutures carried by the needles are preferably stored in four independent magazine compartments within suture magazine 60. Not only is the suture advanced beyond distal wall 45 of the blood vessel, but furthermore, the needles and their respective sutures are inserted interstitial between the suture grabbing elements of distal end 53 of the retrieval device 51.

Figure 10:
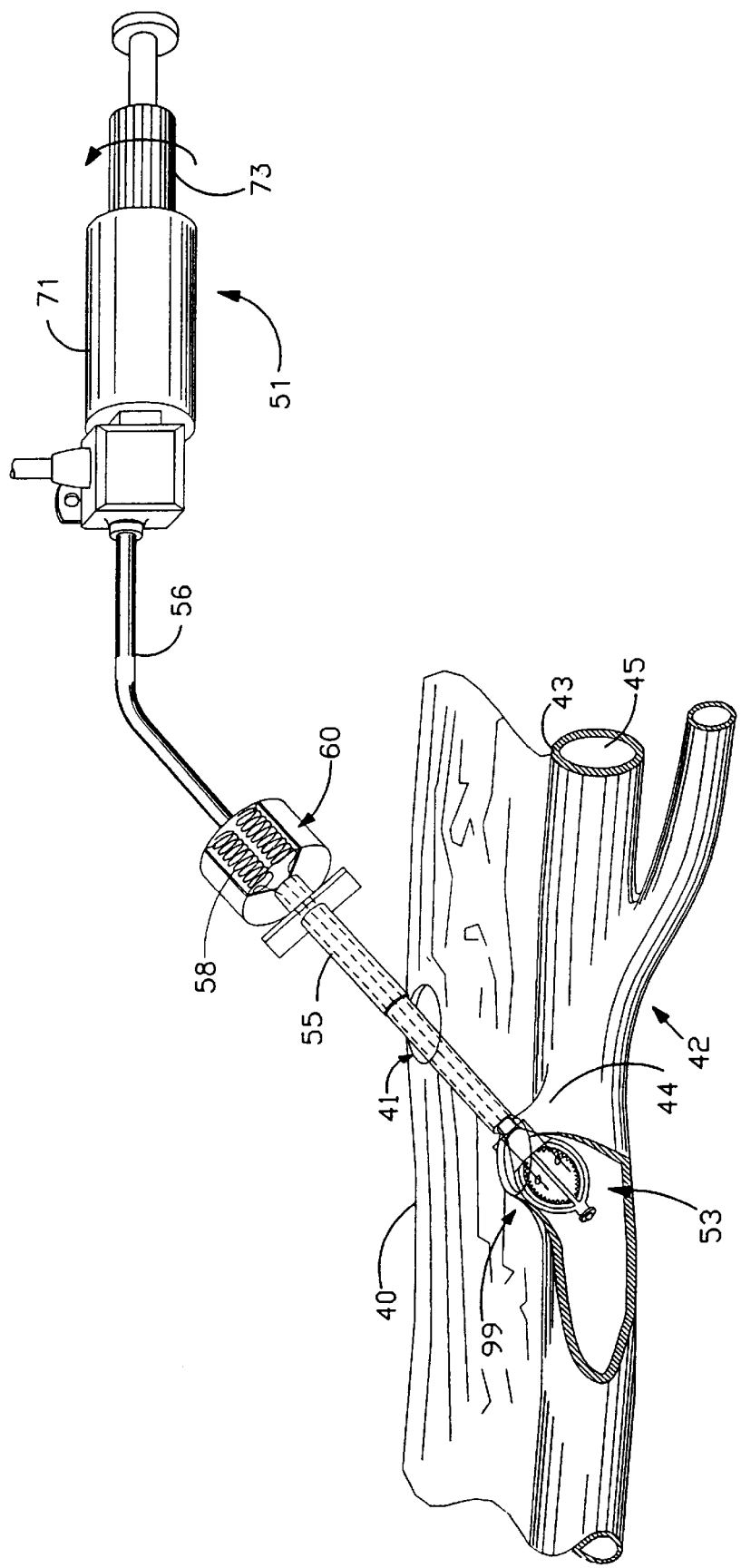

Handle member 73 is attached to the proximal end of retrieval assembly 51 and is rotated with respect to handle 71. This causes rotation of distal end 53 as shown by the arrows (FIG. 10). This rotating, in the preferred embodiment, grabs the sutures carried by the needles. This grabbing action along with the rotation may cause a suture to be pulled out of the magazine compartments (shown partially cutaway) in magazine chamber 60 as it is being drawn into the distal end of the retrieval assembly. A variety of mechanisms, rotational and nonrotational, may be used for this grabbing feature, it being understood that the embodiment illustrated and the embodiments described later are merely exemplary. It should be further noted that the grabbing action occurs beyond opening and occurs on the distal side 45 of the blood vessel wall.

Figure 11:
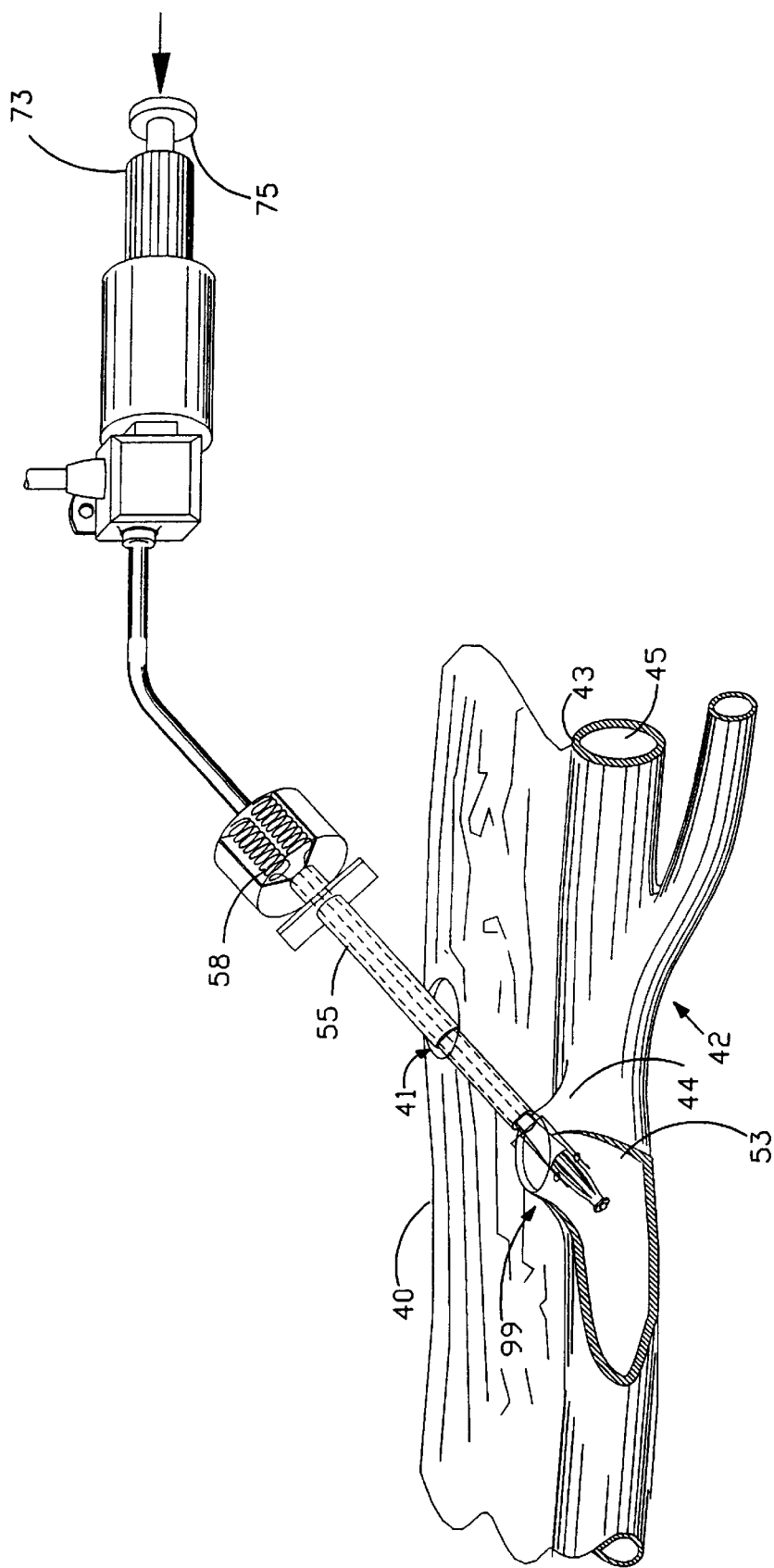

Distal end 53 of the retrieval assembly is then collapsed to allow withdrawal through the lumen of sheath 56 (see FIG. 11). Such collapsing may be accomplished by a variety of mechanisms. In the prefer ed embodiment this is done by longitudinal movement of handle 75 towards handle 73 as illustrated by the arrow in FIG. 11, collapsing the bows of distal end 53 into a cross-sectionally compact mode. In this mode, the sutures remain held by distal end 53.

Figure 12:
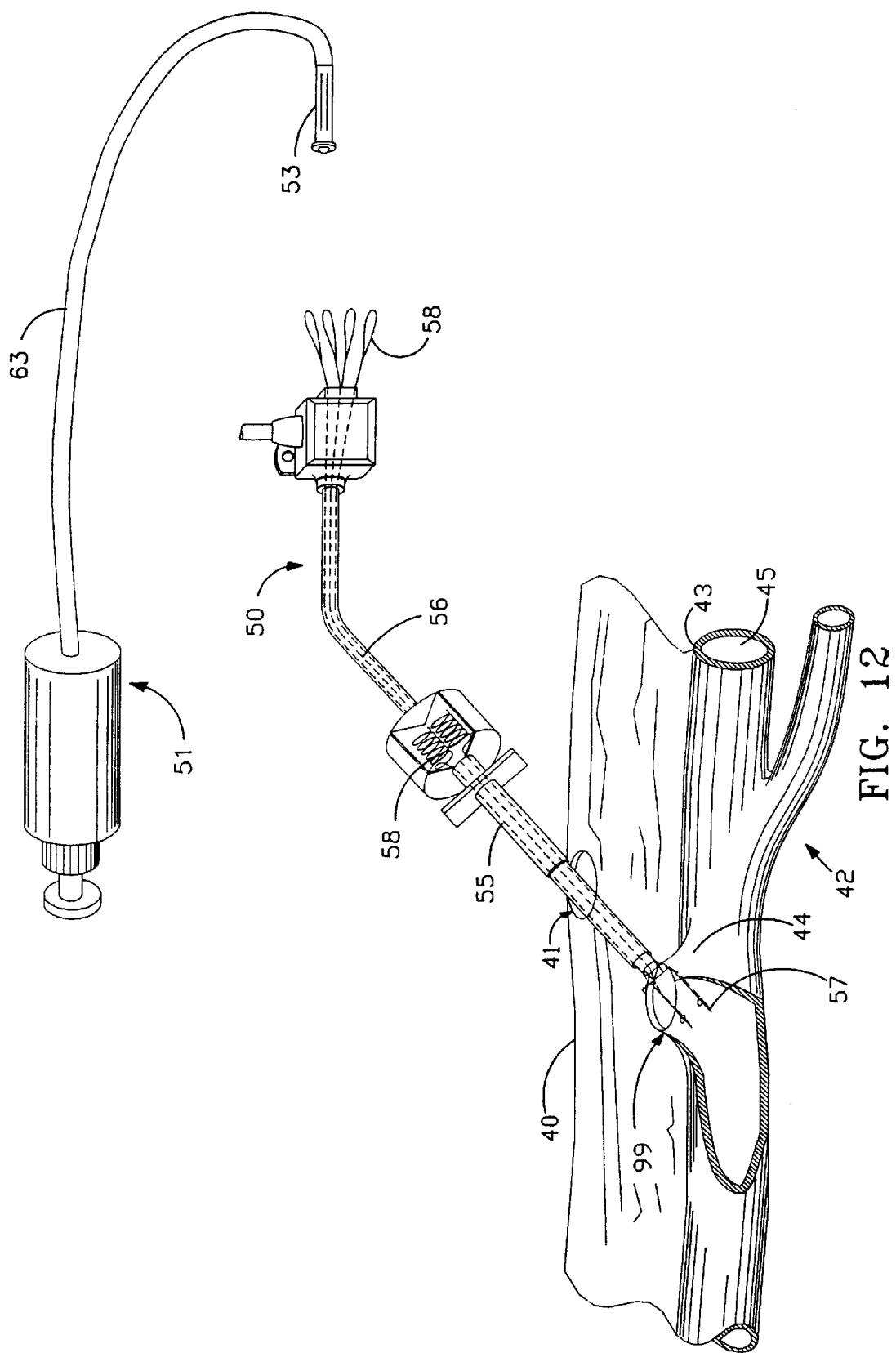

FIG. 12 illustrates retrieval assembly 51 completely withdrawn from apparatus 50. Such withdrawal is accomplished by pulling the retrieval assembly, including elongated tube member 63 and distal end 53, out of the lumen of sheath 56. Since the sutures, such as suture 58, are still connected to distal end 53, the withdrawal pulls the sutures out of magazine 60 distally through the suture locations in the tissue membrane. The sutures are thereby doubled back and pulled outwardly through the lumen of sheath 56.

Figure 13:
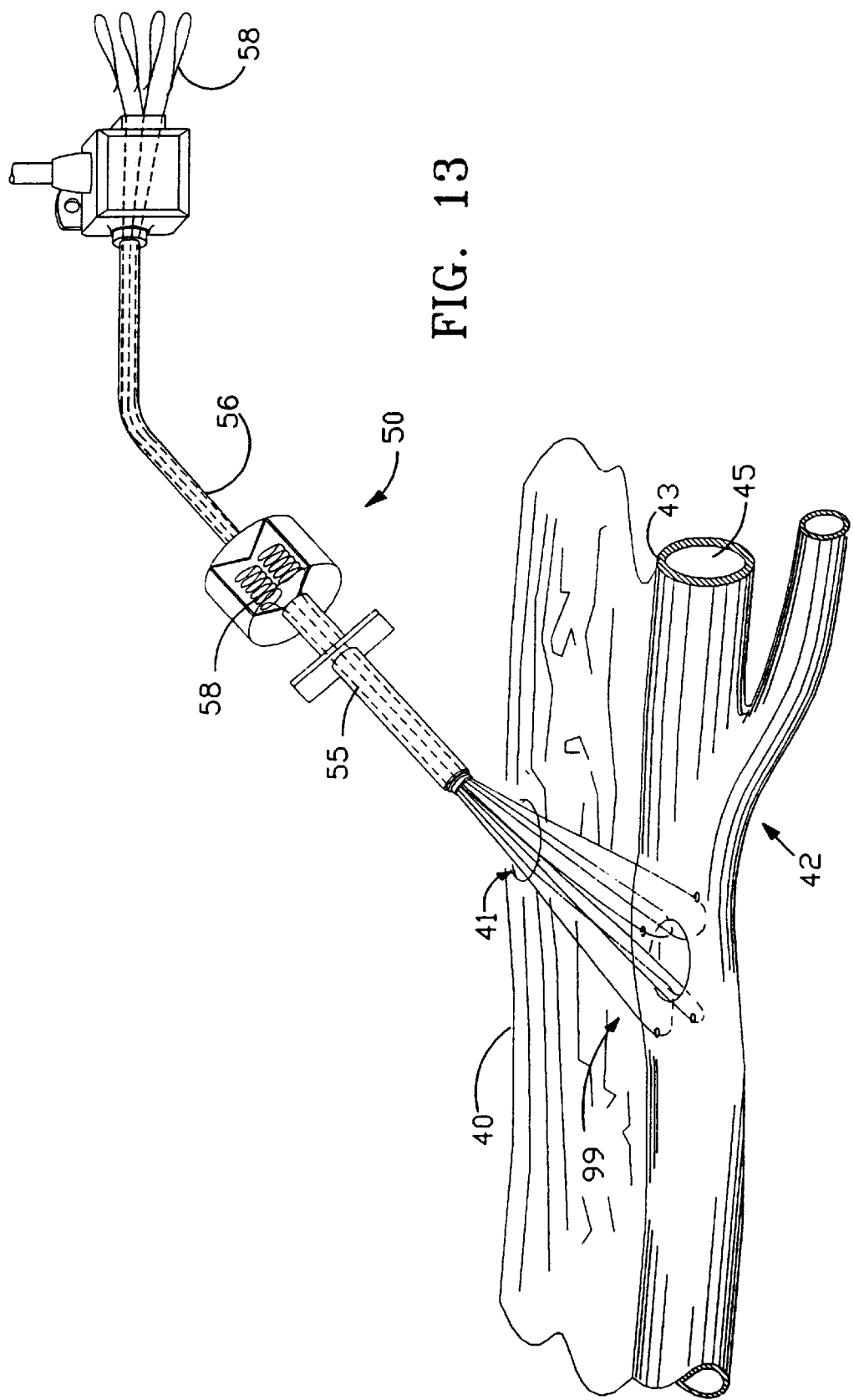

Apparatus 50 is thereafter withdrawn from opening 99 and opening 41 in the patient, carrying the sutures outwardly through opening 41. FIG. 13 illustrates needle guard 55 advanced forwardly, covering the tip of the needles. Such movement of needle guard 55 forwardly is done prior to withdrawal of apparatus 50 and after the needles are retracted into a radially compact mode in a manner inverse to the steps described in connection with FIGS. 6 and 7. Thereafter, apparatus 50 is removed entirely with the sutures being separated (by cutting or otherwise) so that what remains are four lengths of suture (each doubled back) threaded through a respective four suture locations around opening 99 in the blood vessel.

The foregoing method has been described with the simultaneous advancing of four needles and sutures through the tissue membrane. However, it is to be understood that the present procedure may be done with more or less needles and sutures and/or be done with sequential advancing of needles and suture through the tissue membrane. The foregoing method is advantageous in that it may be performed "blind" inside of a patient beneath the surface of the skin of the patient, without the necessity for endoscopic or other viewing. The present invention may also be performed with the assistance of endoscopic equipment in appropriate circumstances. However, such threading operation through opening 41 in the skin without a full cut-down opening of the skin to access and view the opening in the blood vessel or other membrane is extremely advantageous and does not require endoscopic viewing.

Figure 14A:
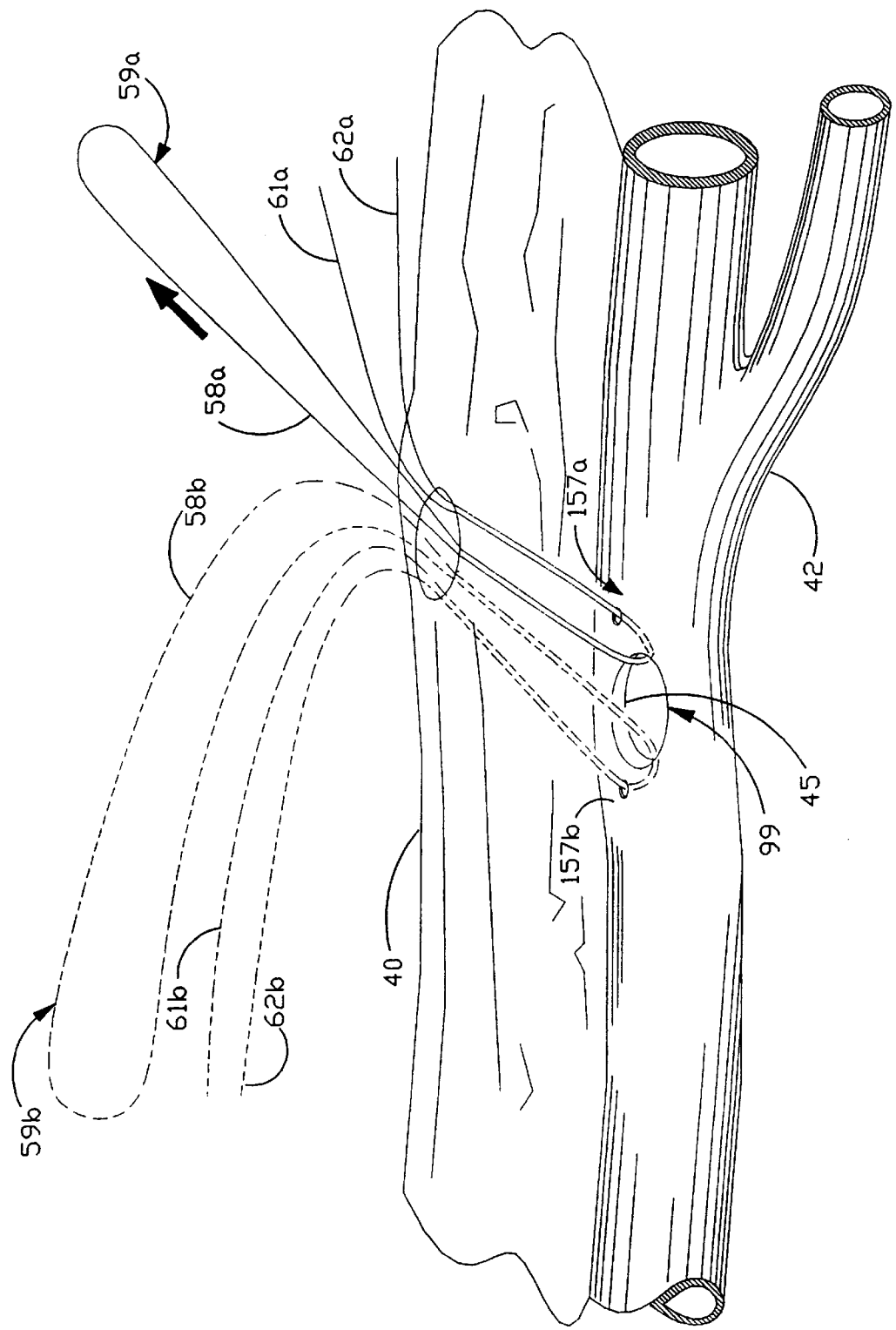
FIGS. 14a–14f sequentially illustrate one embodiment of the method according to the present invention to span sutures across an opening in a tissue membrane.

FIGS. 14a through 14f illustrate one example of a technique to position the sutures as illustrated in FIG. 13 across opening 99 to positively draw the opening closed for healing. In FIGS. 14a–14f, only two (rather than four) sutures are illustrated for purposes of drawing clarity and simplify, it being understood that the same technique may be repeated for the other sutures. FIG. 14a illustrates suture 58a and suture 58b which are vertical surgical sutures (sterilized) which will eventually dissolve in the patient after the wound is healed. Suture 58a is doubled back to form loop 59a at one end with free ends 61a and 62a at the opposite end. Suture 58a is threaded downwardly through suture location 157a from the proximal side of the tissue membrane to the distal side of the tissue membrane, and is doubled back out through opening 99 in blood vessel 42. Similarly, suture 58b is doubled back, forming loop 59b and free ends 61b and 62b. Suture 58b is threaded through suture location 157b.

Free end 61a is pulled through (see the bold arrow in FIG. 14b) suture location 157a and outwardly through openings 99 and 41 so that the suture is no longer doubled back. Then, distal end 61a is inserted through (see the bold arrow in FIG. 14c) loop 59b of the opposite suture 58b. Pulling (see the bold arrows) on both of free ends 61b and 62b (FIG. 14d) causes loop 59b to be drawn downwardly, pulling suture 58a downwardly with it. Continued pulling on free ends 61b and 62b pulls loop 59b upwardly through suture location 157b (FIG. 14e), pulling suture 58a upwardly through suture location 157b.

Figure 14B:
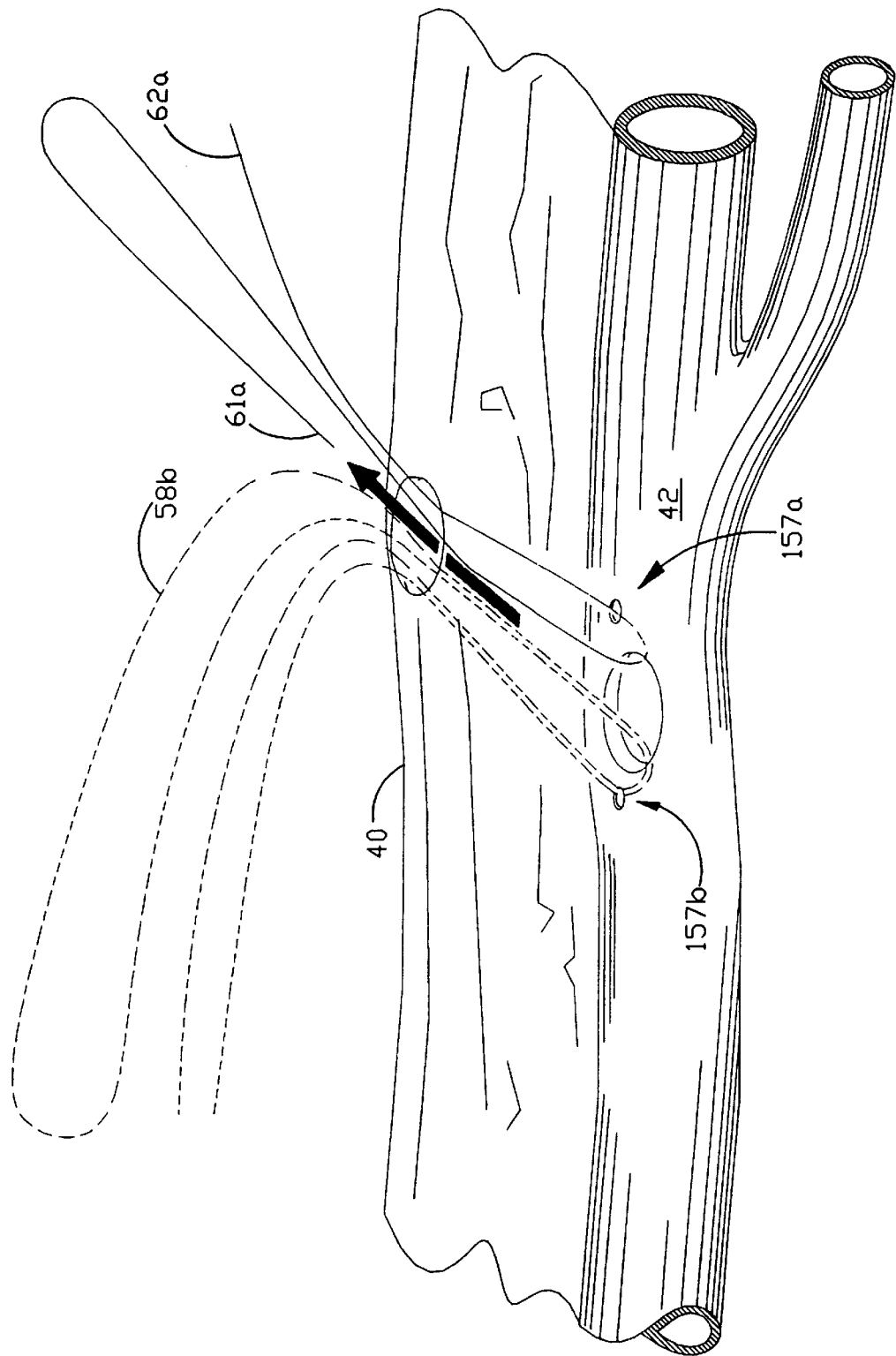
Figure 14C:
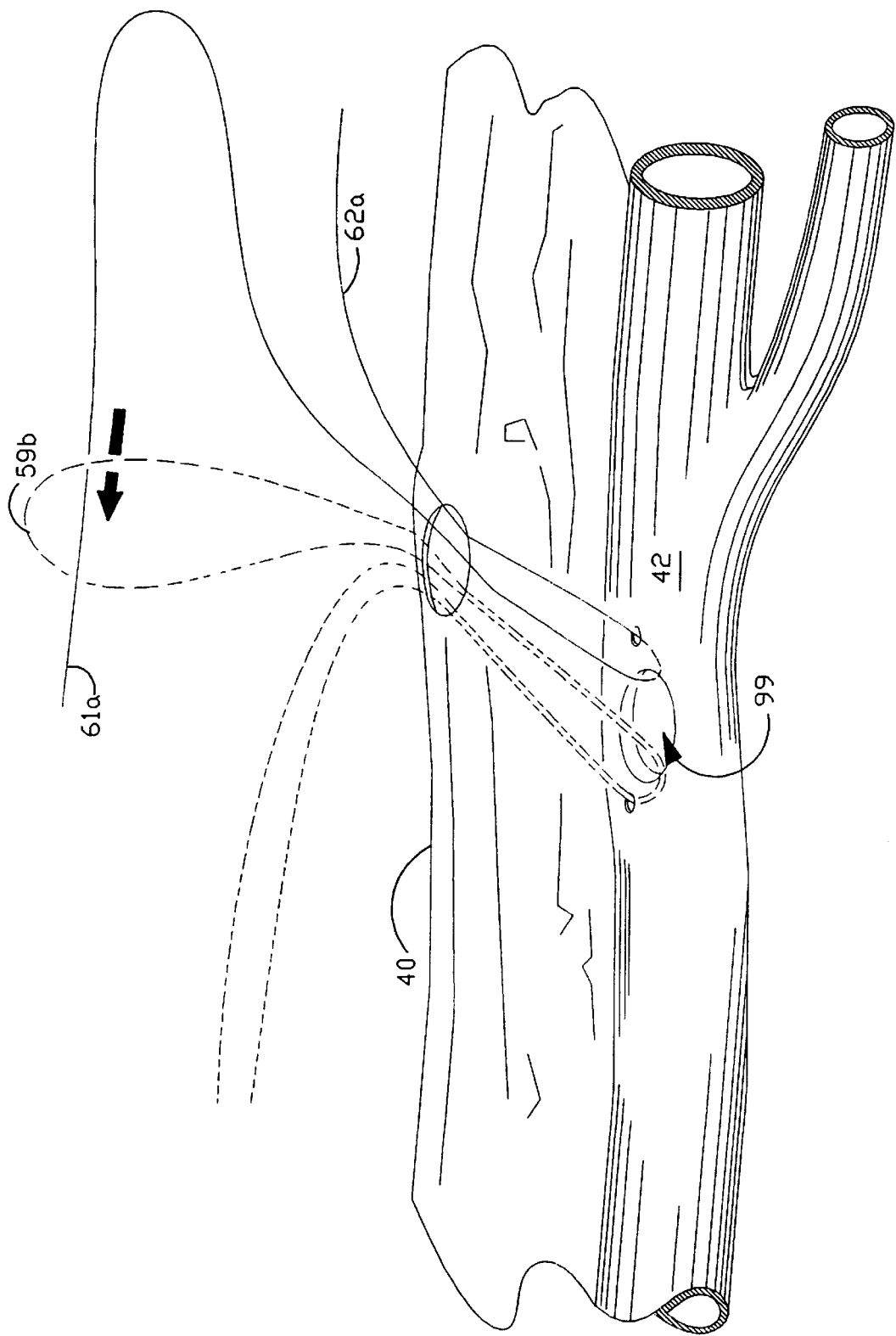
Figure 14D:
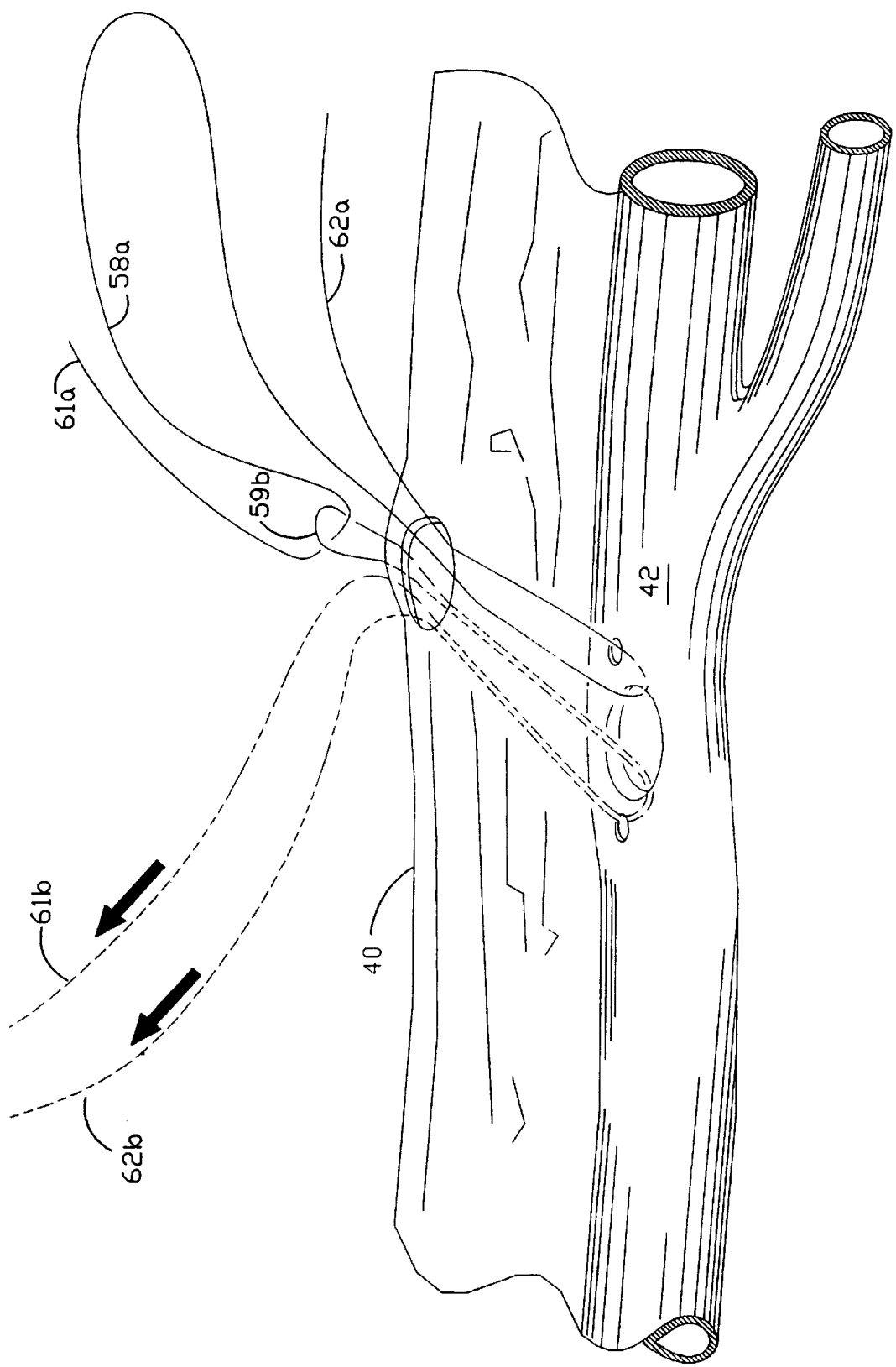
Figure 14E:
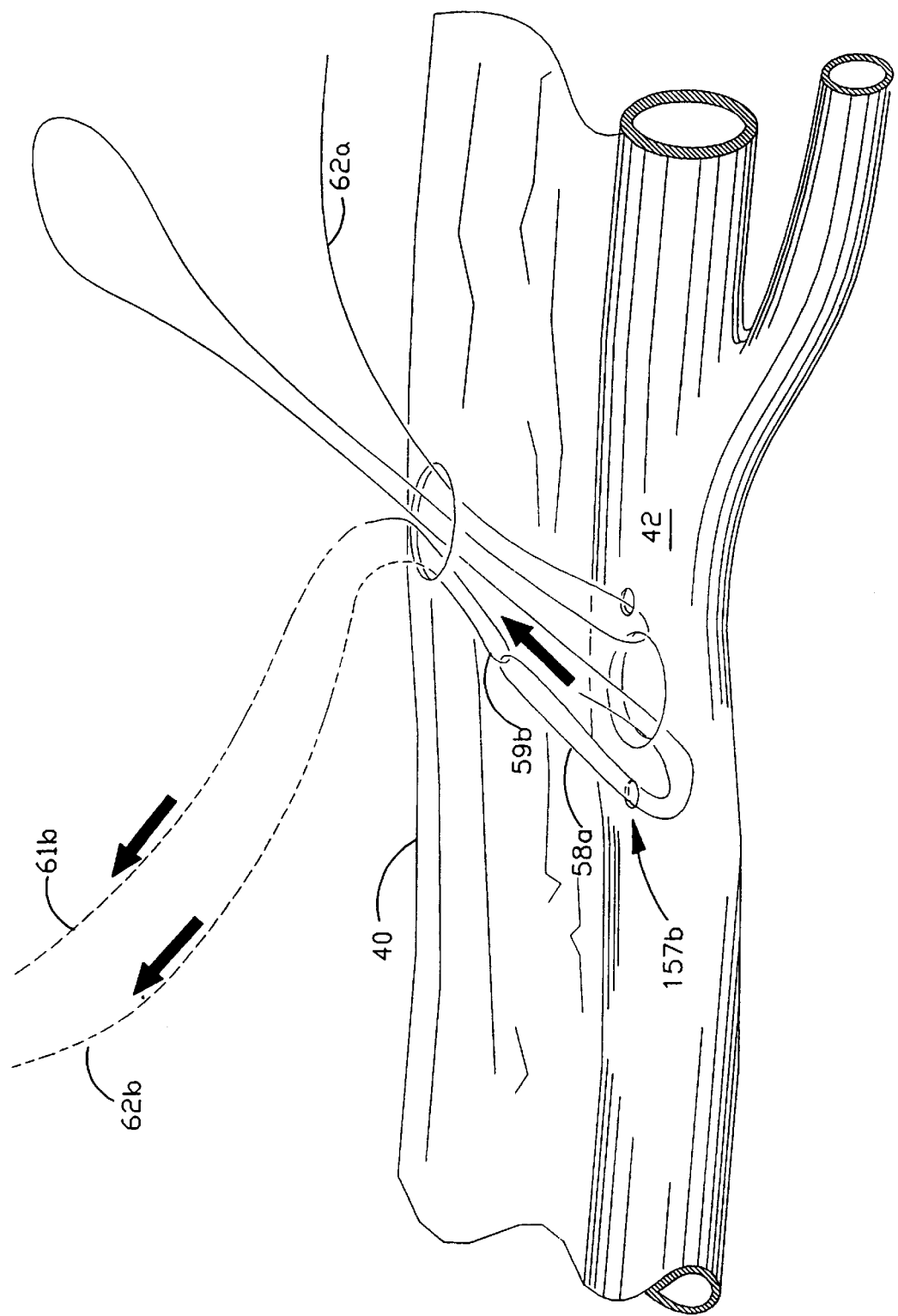
Figure 14F:
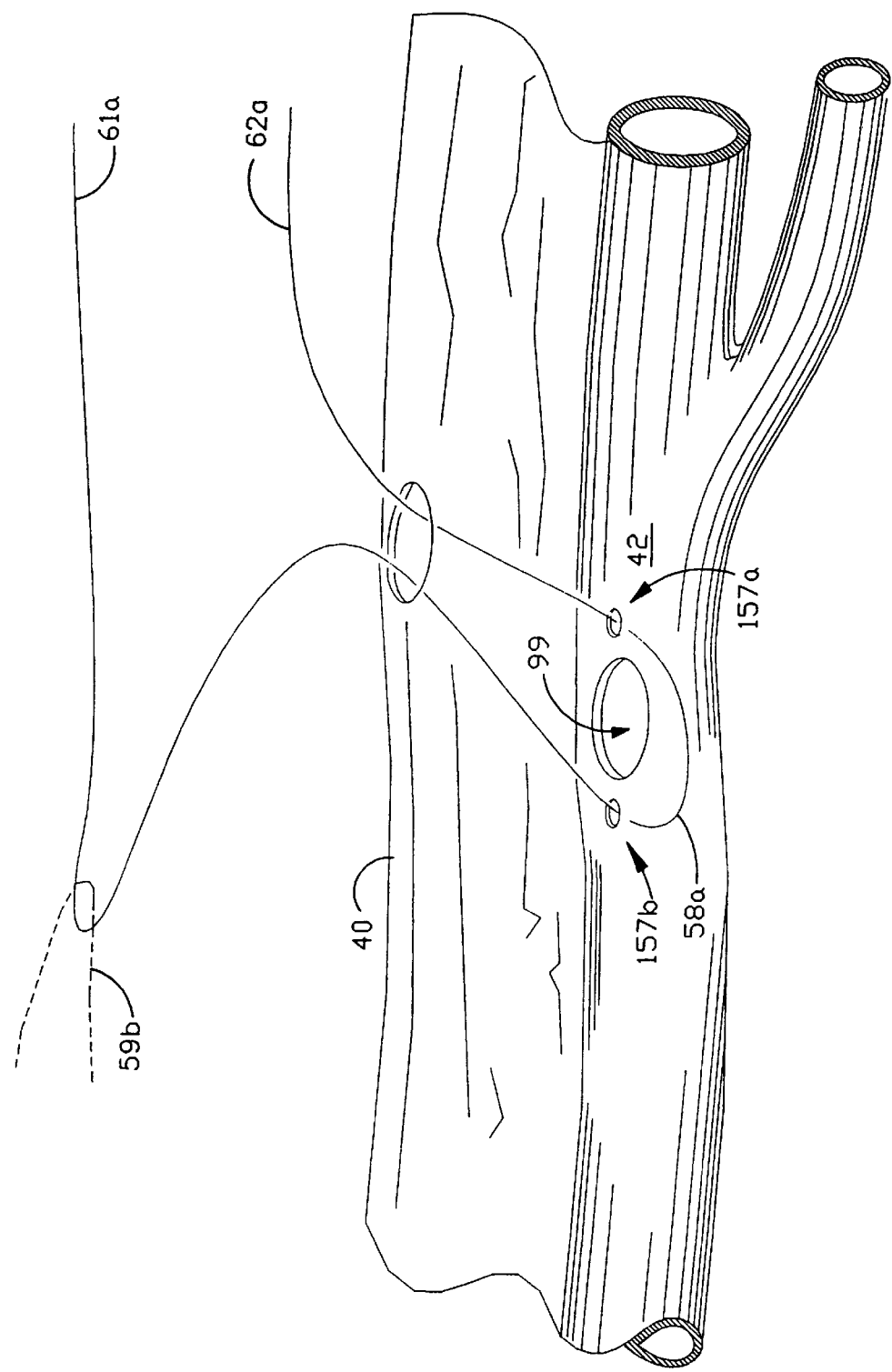

FIG. 14f illustrates suture 58a passing through the tissue membrane at suture locations 157a and 157b, spanning diametrically across opening 99. Thereafter, suture 58a is drawn tight, such as by advancing or by "throwing" a suturing knot (e.g. an overhand knot) across opening 99, and positively drawing it closed. Such knot techniques and knot throwing may be accomplished with the aid of a pusher to advance the suturing knot downwardly towards opening 99.

It is to be understood that the foregoing threading illustrated in FIGS. 14a–14b is merely exemplary, and other techniques may be used, including techniques to provide a suture circumferential around opening 99 in a purse string configuration. After opening 99 is drawn closed, opening 41 is closed in the conventional manner and the patient is allowed to heal.

FIGS. 15a–17d illustrate in greater detail the needle advancing apparatus 50 and the retrieval assembly 51 previously described. Sheath 56 forms a central core of apparatus 50. Sheath 56 comprises a side wall defining a central lumen 56a passing all the way through assembly 50. Although as illustrated sheath 56 has a single lumen, it is contemplated that the present invention may be utilized with a multi-lumen sheath and/or device having endoscopic capabilities. Sheath 56 has housing 56d forming a chamber therein mounted at its proximal end. Housing 56d has a seal 56b mounted therein. This seal may be a variety of designs, but preferably is an elastomeric gasket body, such as silicone rubber, having slits and/or other openings therein to allow elective insertion and removal of medical instruments, such as guide wires, catheters and other such devices, while maintaining a fluid tight seal therearound. In this way, blood or other bodily fluid is prevented from leaking out, and unwanted air is prevented from entering into the body.

Housing 56d further has a side port (optional) 56e which ordinarily will have a stop-cock or other closure mechanism (not shown). In this way, catheter 56 may act as a hemostasis cannula to remain indwelling in the blood vessel 42 throughout the prior medical procedure.

Figure 15C:
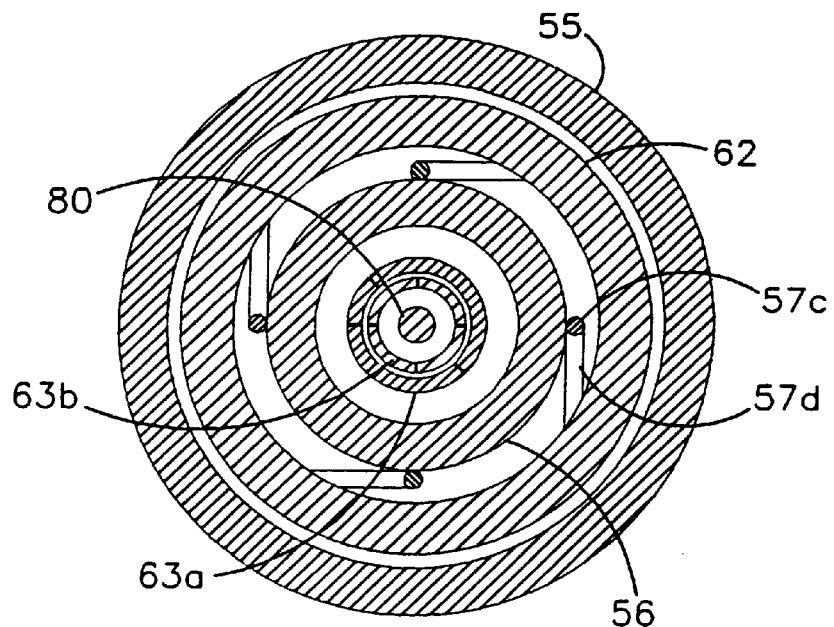
FIG. 15c is a cross-section looking in a distal direction as if taken along lines 15c—15c of FIGS. 15a and 16 collectively.

Apparatus 50 further includes a tubular member 62 surrounding sheath 56 and providing a housing for holding the four needles, such as needle 57. Needle 57 is shown in isolation in FIG. 15b and includes needle tip 57a at its distal end, a proximal portion 57b, and a central portion 57c therebetween. Central portion 57c defines a longitudinal axis of rotation. Proximal portion 57b is connected to the central portion by crank portion 57e. Similarly, the needle tip is eccentric to the axis defined by central portion 57c since it is connected to the central portion by crank portion 57d. As illustrated in FIG. 15a, needle 57 is mounted with the central portion 57c rotationally movable within tubular member 62, and with proximal portion 57b mounted in thread magazine 60. Thread magazine 60 is rotationally movable over a ninety degree arc with respect to tubular member 62, and such movement causes a cranking action of needle 57 ranging from fully compact to fully deployed, optionally with locks in each position. Such cranking action causes rotation of the central portion 57c which, in turn, causes cranking or swinging of crank portion 57d and needle tip 57a inwardly and outwardly with respect to sheath 56. In this way, with needle guard 55 withdrawn as illustrated in FIG. 15a, needle tip 57a, along with the needle tips of the other three needles, is cranked to swing radially inwardly and outwardly with respect to sheath 56 to allow positioning of the needles for insertion through the tissue membrane around the hole. Such cranking action is illustrated comparatively between FIG. 17a and FIG. 17c, and between FIGS. 17b and 17d. FIG. 5c illustrates a cross sectional view, looking distally, through apparatus 50 and assembly 51 with the needles in a compact mode.

Suture 58 is housed in suture chamber 65 within suture magazine 60. In FIG. 15a, the remaining suture magazines are shown empty for illustration purposes, it being understood that in operation each carries suture for its respective needle. Suture chamber 65 includes a pair of suture openings 66 through which the suture is pulled as the suture is advanced through the tissue membrane of the patient. The suture passes between sheath 66 and tubular member 62 and is carried through an eyelet at the tip of its respective needle. Alternative needle constructions may also be used, such as a hollow needle cannula carrying suture downwardly through the center of the cannula and doubled back on the outside of the cannula away from the cutting edge.

The needle assembly and member 62, along with the needle magazine 60, may be modified to allow placement around sheath 56 seen after sheath 56 is in place in the patient, as an option to the illustrated version in which tubular member 62 is positioned around sheath 56 prior to insertion of sheath 56. For example, member 62 may be longitudinally split and provided as two mating parts, such as a clam shell, around the outside of sheath 56 (not shown).

FIG. 16a illustrates a partially cutaway side view of retrieval assembly 51. Retrieval assembly 51 has a handle assembly on the proximal side thereof opposite of distal member 53, with elongated tubular member 63 therebetween. Elongated tubular member 63 may comprise a catheter having a wire or other tension member 80 disposed in its central lumen. Distal end 53 has a plurality of inner bows and outer bows such as bow 54. These bows are formed in one embodiment by slits in the wall of tubular member 63a (outer bow) and slits in the wall of tubular member 63b (inner bows). Each bow has a distal end 53d, a proximal end 53p, and a central portion 53c therebetween. Tension member 80 is attached to the distal end 53d by connection 80a. As illustrated, each inner bow may have serrations along its inside edge. When tension member 80 is pulled towards the proximal end of assembly 51, it draws the distal ends of the bows toward the proximal ends of the bows, causing the central portions to bulge outwardly in a radial direction.

Such bulging is illustrated by comparing FIG. 17c (end 53 in a contracted position) with FIG. 17a (end 53 in an expanded position). In the expanded position, serrations on the inner bows are exposed to help grab the sutures.

Movement of tension member 80 with respect to elongated tubular body 63 may be accomplished in a variety of ways, one of which is illustrated in FIG. 16a. Specifically, handle 75 is moved longitudinally with respect to handle 71 and handle 73 to cause such relative movement. Handle 75 is mounted and slidable longitudinally within handle 73. Handle 75 is urged axially away from handle 73 by compression spring 77. Handle 75 is connected to tension member 80, whereas handle 73 is connected to elongated member 63b. Pin 76a secured to handle 75 is slidable within z-shaped slot 76b in handle 73. In this way, relative movement between the handles is at a predetermined and controlled distance with a positive locking feature. Furthermore, handle 73 is rotatable within handle 71. Specifically, handle 73 includes a circumferential groove 72b which rides around radially inward detent 72a, allowing radial rotation but not allowing axial movement between handles 73 and 71. Such rotation is further controlled and limited by pin 74a abutting stop member 74b. The rotational position of distal end 53 is thereby limited and is indexed at a known position. By maintaining handle 71 stationary the outer bows of tubular member 63a (affixed thereto) are maintained stationary; whereas rotation of handle 73 within handle 71 cause the inner bows of tubular member 63b to rotate inside of the stationary, outer bows. The rotating inner bows have serrations which grab the suture while the outer bows remain stationary to shield surrounding issue from abrasion or other damage.

Figure 15D:
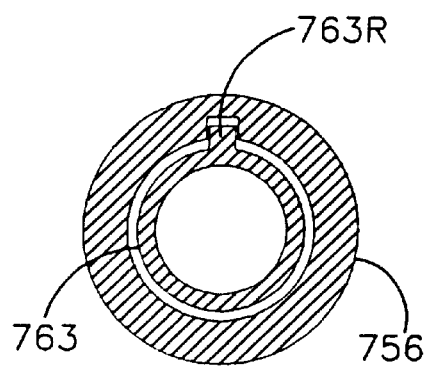
FIG. 15d is a partial cross-sectional view of an alterative embodiment of a tubular member of assembly 51 within the sheath of apparatus 50.

Through visual indexing markings, or actual physical forced alignment, the relative axial position between the bows of distal end 53 of retrieval assembly 51 may be predetermined with respect to the needles 57 of assembly 50. As a result, when the needles are advanced through the tissue membrane, the operator may ensure that the bows are placed to allow interstitial insertion of the needles between the outer bows. It is contemplated that this indexing mechanism may be facilitated by providing apparatus 50 in a sterilized kit with retrieval assembly 51. For example, tubular member 63 and sheath may be modified as illustrated in FIG. 15d with tubular member 763 having a longitudinal outer rib 763R which slides in a corresponding longitudinal inner groove in sheath 756. A mating interaction may be provided between retrieval assembly 51 and apparatus 50, such as by mating interaction between the distal end of handle 71 and housing 56d to maintain alignment of the needles and the bows.

Figure 16C:
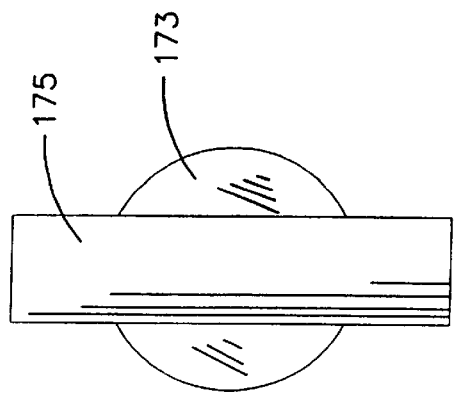
FIG. 16c is a rear view of the proximal end of the assembly of FIG. 16b.
Figure 16B:
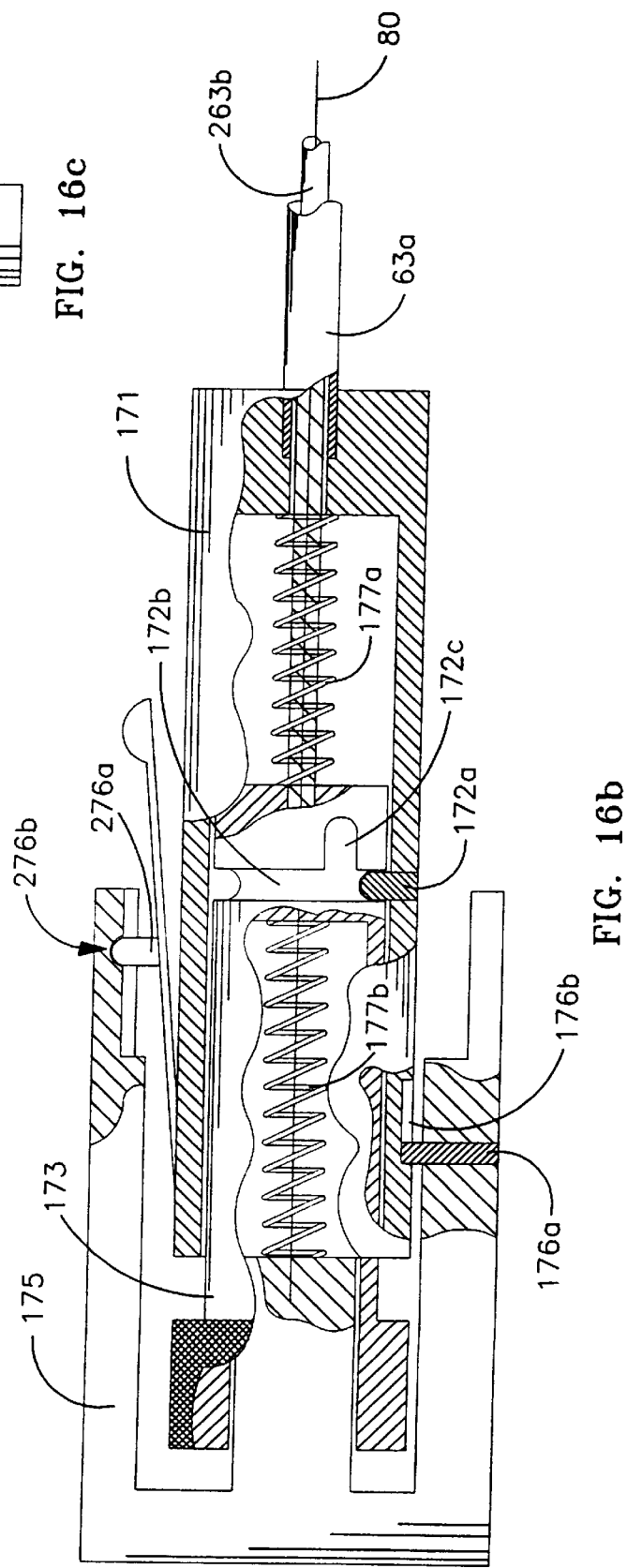
FIG. 16b is a partially cut away side view of another embodiment of a suture retrieval assembly according to the present invention.

FIGS. 16b and 16c illustrate an alternative embodiment of the retrieval assembly of the present invention. The structure noted by reference characters are similar to those used in connection with FIG. 16a except that a "1" or "2" is set forth in the hundredths digit of the corresponding reference character. For example, the handle 175 as in FIG. 16b and 16c is analogous to handle 75 in FIG. 16a. The retrieval assembly has three key components, handle 171, handle 173 and handle 175. Handle 171 is affixed to tubular member 63a; handle 173 is affixed to tubular member 263b; and, handle 175 is affixed to tension member 80.

Handle 175 moves rearwardly (proximally) with respect to handle 171, thereby causing tension member 80 to be pulled in tension rearwardly (proximally) with respect to tubular member 63a. Such rearward movement is actuated by withdrawing pin 276a from recess 276b, such as by radially inward movement of the lever to which pin 276a is attached. Such withdrawal of the pin from the recess causes handle 175 to move rearwardly due to the forces acted upon by it by compression spring 177b. Pin 176a of handle 175 rides in longitudinal slot 176b of handle 171 to maintain alignment and to restrict relative travel distance. Tension is thereby exerted in tension member 80, causing the distal end of the retrieval assembly to expand as described in connection with FIG. 16a. Movement of handle 175 forward causes the distal end to collapse to allow passage through sheath 56.

Handle 173 is first advanced and then rotated. Handle 173 is longitudinally movable with respect to handle 171, thereby causing longitudinal movement of tubular member 263b with respect to tubular member 63a. Handle 173 may be advanced forwardly (distally) with pin 172a riding in longitudinal slot 172c overcoming the bias of compression spring 177a causing extension of tubular member 263b. Handle 173 is rotatable with respect handle 171, causing tubular member 263b to rotate with respect to tubular member 63a. Rotation occurs with pin 172a riding in circumferential groove 172b. Rotation of handle 173 and the resulting rotation of tubular member 263b causes rotation of the snagging mechanism within the bows of the distal end of the retrieval assembly. Longitudinal withdrawal of tubular member 263b causes withdrawal of the snagging mechanism at the distal end of the assembly, such as described further in connection with FIGS. 19 and 20 below.

FIGS. 17a–17d provide schematic comparisons of the moving parts of the present invention in different positions. For example, FIG. 17a and FIG. 17b show needle guard 55 retracted or withdrawn, with needles 57 in a radially expanded mode and with distal end 53 of the retrieval assembly like wise in an expanded mode. Needle guard 55 includes handle 55a attached thereto to facilitate manual sliding along the outside of tubular member 62. Conversely, FIG. 17c and FIG. 17d illustrate needle guard 55 advanced in a sheathed position with the needles 57 in a radially retracted position and with a distal end 53 of the retrieval assembly likewise in a contracted position. Comparison between FIGS. 17b and 17d illustrates the cranking action of cranking portion 57e of the needles. Note further that these two figures illustrate sutures in dual coils in all four chambers of the suture magazine.

Figure 18:
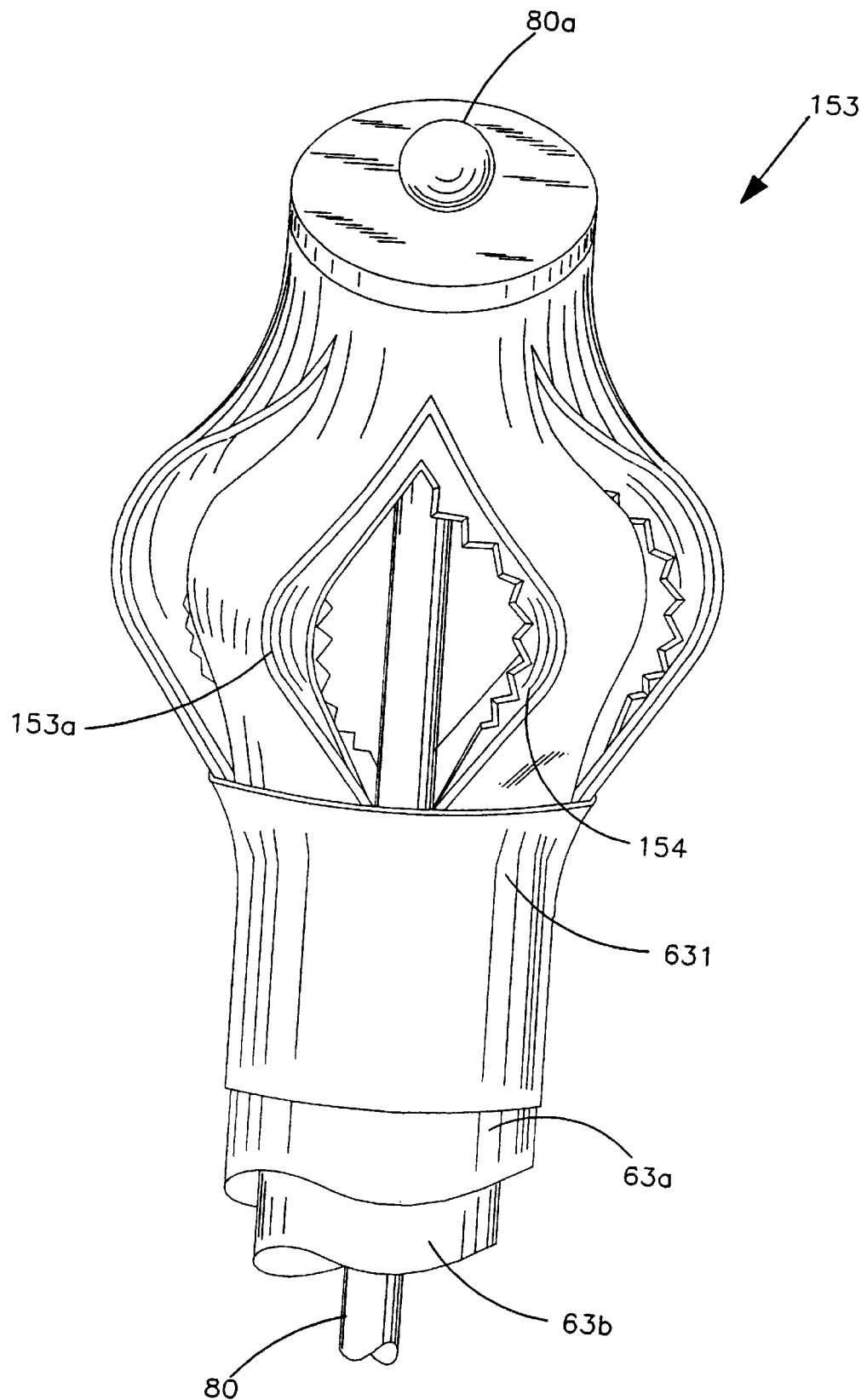
FIGS. 18–22 illustrate alternative embodiments of the distal end of the retrieval assembly.

FIG. 18 shows distal end 153 with outer bow 153a and inner serrated bow 154. Serrated bow 154 is formed from slits in flexible tubular member 63b having at least one serrated edge along each bow, as illustrated. Serrated bow 154 deflects outwardly similarly to the action of bow 153a when tension member 80 is pulled proximally with respect to elongated member 63a. In such expanded state, end 153 comprises four inner bows within four outer bows. The inner bows rotate as previously described with respect to the stationary outer bows. A sealing member, such as elastomeric boot 631, preferably is provided at the proximal base of the outer bows. This seal 631 function to seal the opening which is being closed during the procedure so fluid, such as blood, is prevented from flowing out. Seal 631 expands as the bows are expanded sufficiently to seal the opening.

Figure 19:
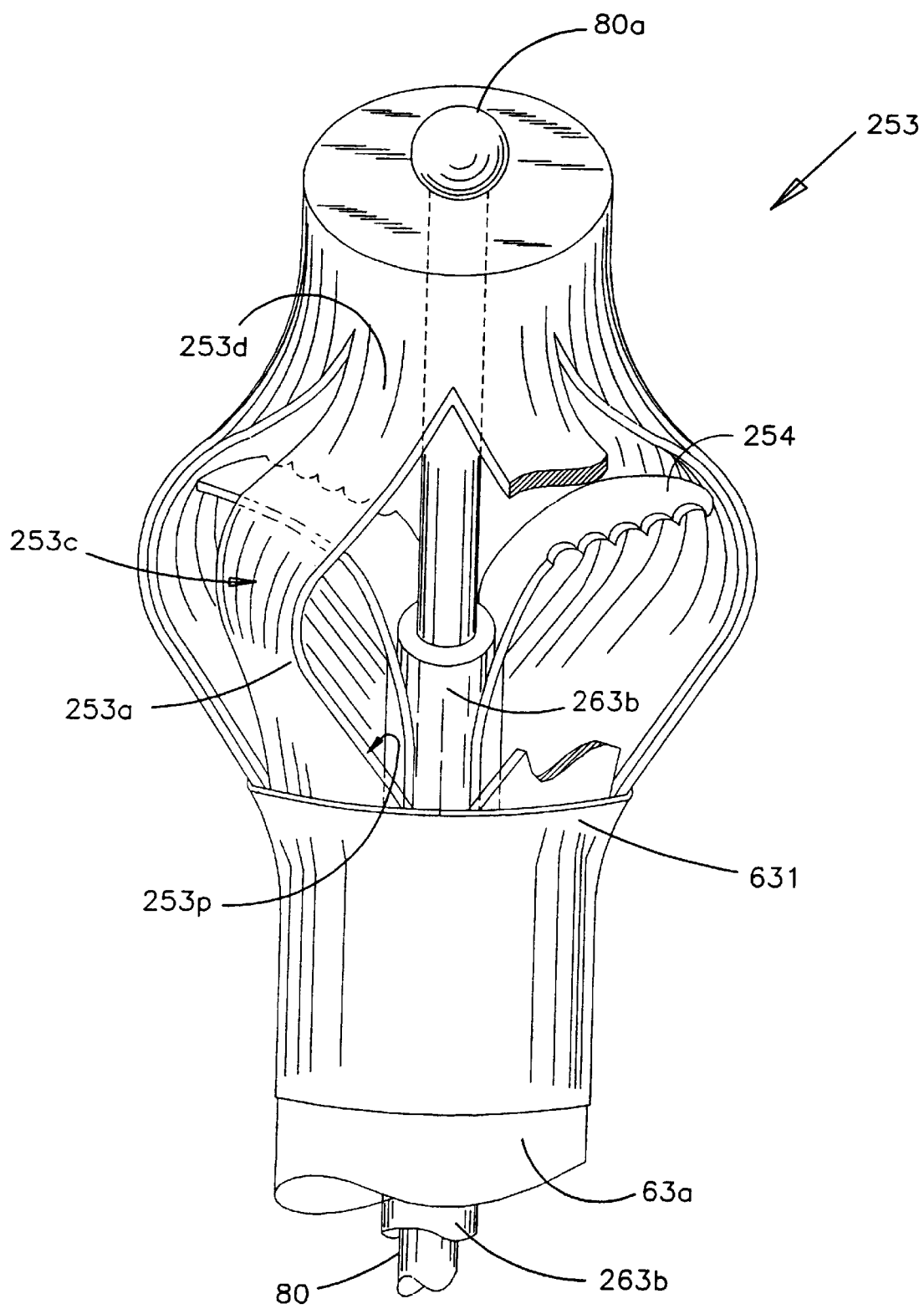

Referring to FIG. 19, an alternative embodiment of the distal end of the retrieval device is shown as distal end 253, with one of the bows partially cutaway for drawing clarity. The bows, such as 253a, are formed from slits in elongated tube 63a which surrounds tension member 80. Bow 253a includes distal end 253d, proximal end 253p and central portion 253c. Two serrated members, such as serrated member 254, are rigidly attached to a collar 263b, which is an end of tubular member 263b described in connection with FIG. 16b above, and which is mounted over tension member 80.

Rotation of the collar/tubular member 263*b* and serrated member 254 within fixed distal end 253 causes snagging and grabbing of sutures which are attached to the needles (previously described) positioned interstitially between the bows. Seal 631 is provided and functions as described above. Pulling on tension member 80 and its end piece 80*a* cause the bows to expand. Collar 263*b* may be a portion of an elongated tube which is axially movable to retract serrated members 254 within the outer bows as described with FIG. 16*b*.

Figure 20:
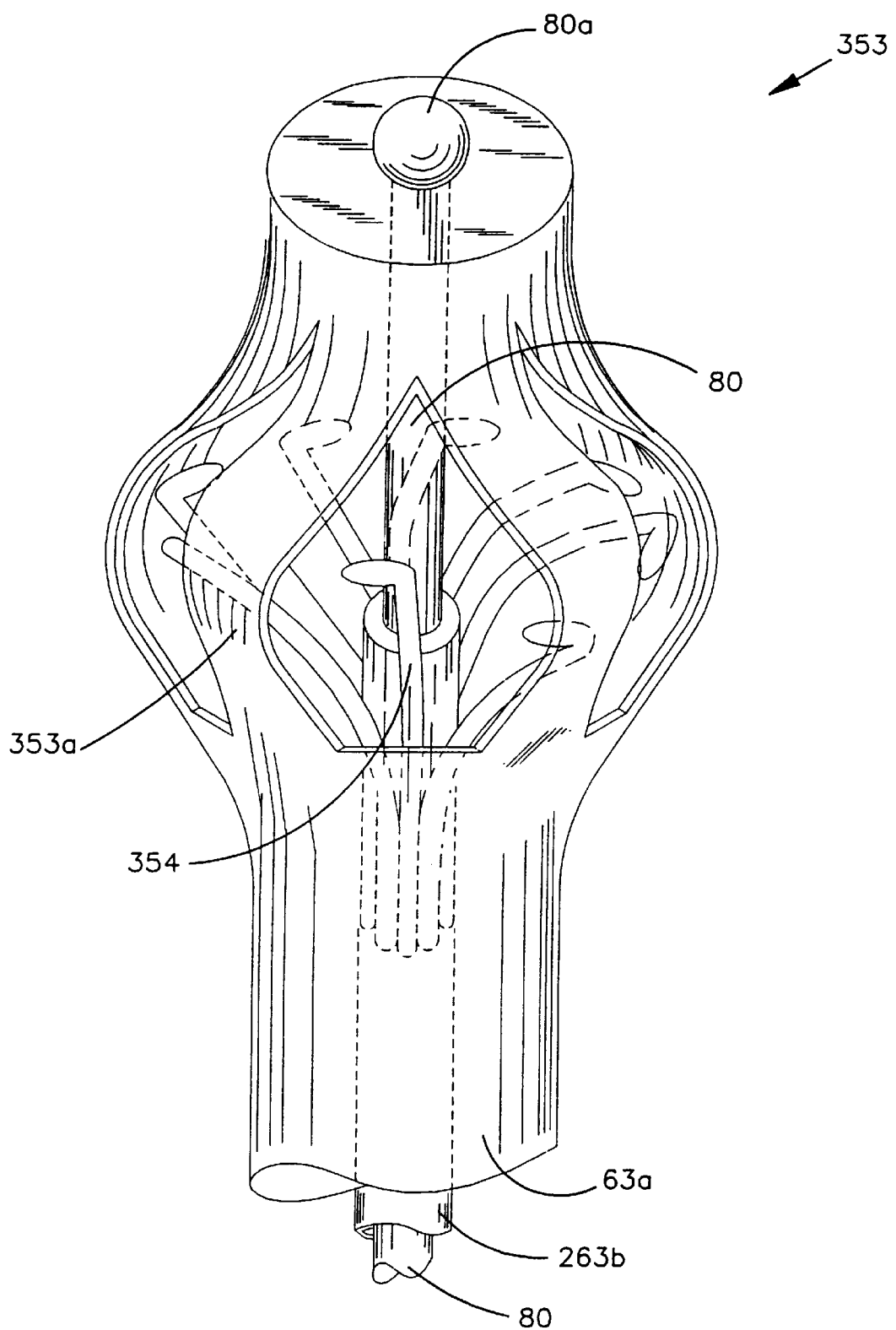

As a further alternative, FIG. 20 illustrates distal end 353 with bow 353*a* surrounding prong 354. As illustrated, other prongs (shown in phantom lines) are mounted over tension member 80 to grab and snag suture. Note that optionally, instead of a boot 631 providing a seal, the bow configuration is altered to provide a frustoconical sealing surface around the base of the outer bows. As with the device of FIG. 19, tubular member 263*b* may be rotated and retracted to withdraw prongs 354 into a collapsed state.

Figure 21:
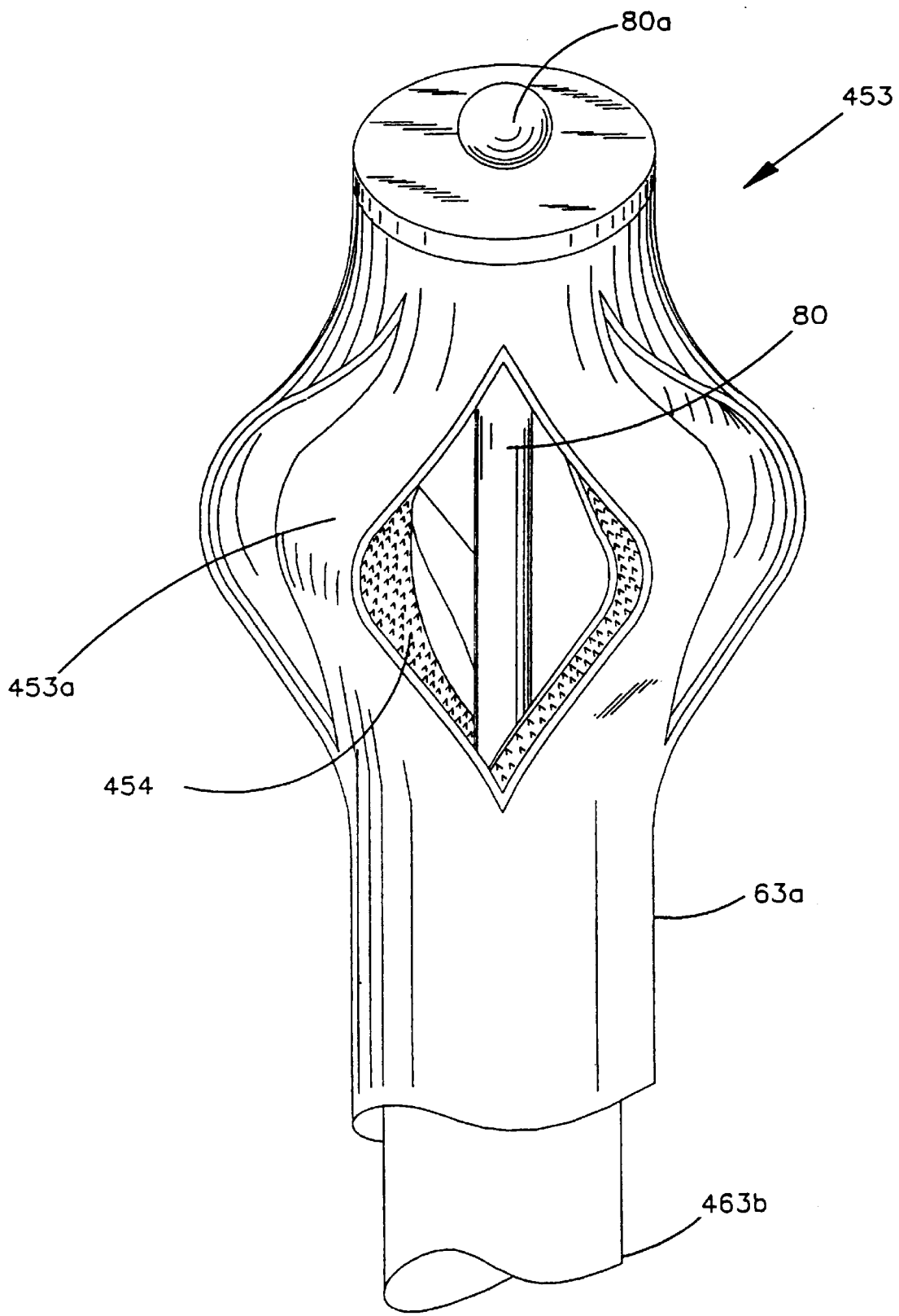

FIG. 21 illustrates yet another embodiment, in which distal end 453 includes a plurality of bows, such as bow 453*a,* formed in an outer sheath 63*a*. Sheath 63*a* is mounted around elongated member 463*a* which in turn is mounted around tension member 80. Inside the outer bows is a second set of bows, such as bow 454. These inner bows 454 may be of a hook fabric material, such as Velero® material. Such hook material may be used in connect on with multi-filament and/or monofilament suture material which acts as nap material to snag on the hook material of bow 454 as bows 454 are rotated with the outer bows. A seal may optionally be added.

Figure 22:
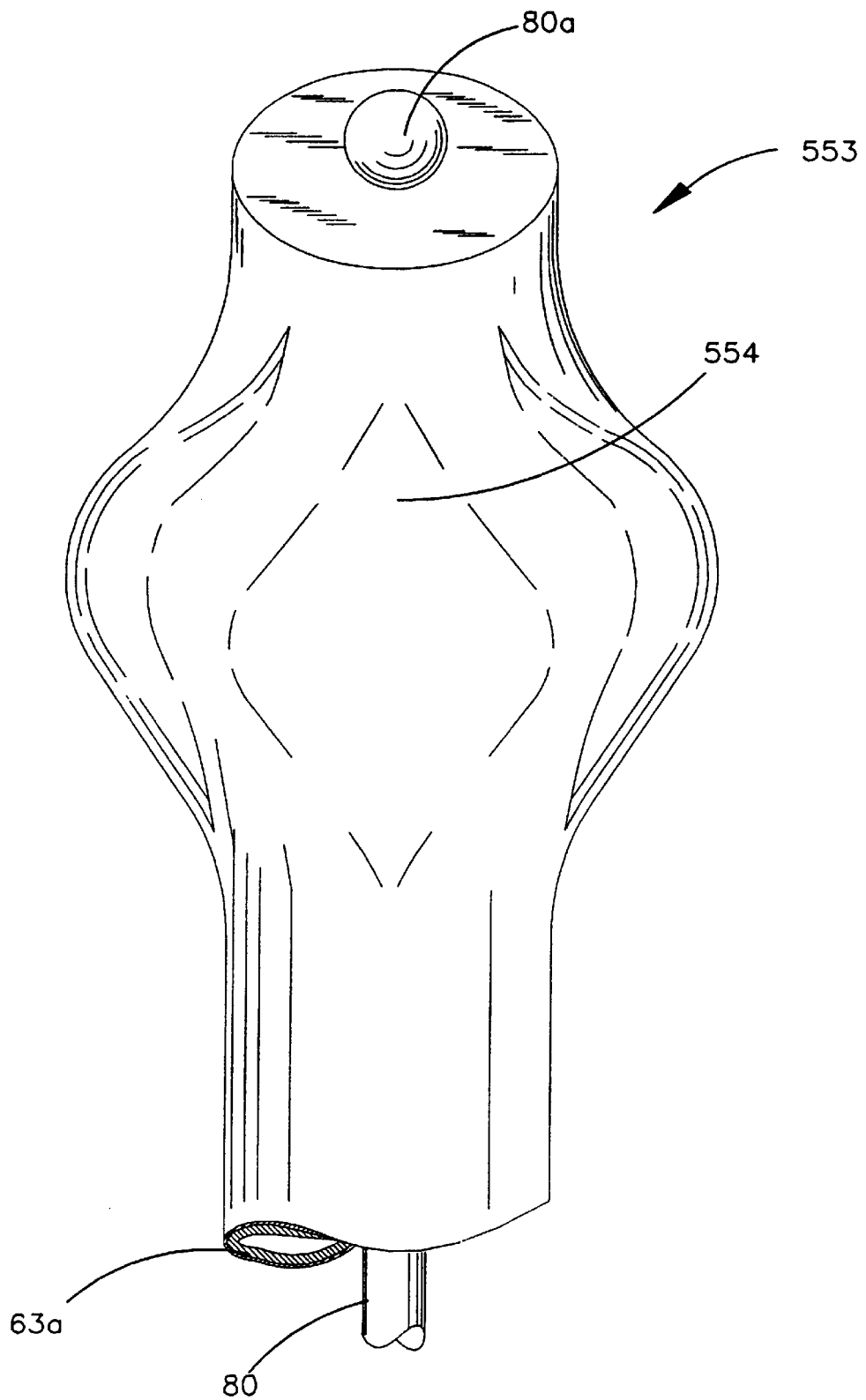

As stated, other approaches to grasping the suture material on the distal side of the membrane to be closed may be provided. FIG. 22 illustrates distal end 553 with a membrane 554 of an elastomeric material, such as latex rubber, stretched around the outside of the expandable bows of member 63*a* and/or as part of a balloon. It has been found that when the interstitial needles penetrate through such latex rubber with the suture, the suture remains in place in the latex, even upon removal of the needles. A rotational inner member is typically not required, although optionally may be provided. Membrane 554 also acts as a hemostasis seal.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for capturing an edge of an opening in a blood vessel membrane with suture, said method comprising:

penetrating a first needle in a distal direction through the membrane at a first site adjacent to the opening, wherein the needle carries a first length of suture into a lumen of the blood vessel; and retrieving the first length of suture from the blood vessel lumen and pulling the suture through the opening.

2. A method as in claim 1, further comprising:

penetrating a second needle in a distal direction through the membrane at a second site adjacent to the opening, wherein the needle carries a length of suture into a lumen of the blood vessel, wherein the second site is peripherally spaced apart from the first site; and retrieving the second length of suture from the blood vessel lumen and pulling the suture through the opening.

3. A method as in claim 2, wherein the retrieving steps comprise introducing a retrieval device through the opening in the blood vessel membrane into the blood vessel lumen, grabbing the first and second lengths of suture with a distal end of the retrieval device, and pulling the distal end of the retrieval device proximally through the opening.

* * * * *